United States Patent
Barnes et al.

[11] Patent Number: 6,027,938
[45] Date of Patent: Feb. 22, 2000

[54] MICROPATHOLOGICAL PATIENT REPLICA BASED ON UNADULTERATED WHOLE BLOOD

[76] Inventors: Allen C. Barnes; Janice S. Barnes, both of 400 Newport Center Dr. Suite 410, Newport Beach, Calif. 92660

[21] Appl. No.: 09/045,291

[22] Filed: Mar. 20, 1998

Related U.S. Application Data

[63] Continuation-in-part of application No. 08/826,429, Mar. 20, 1997, abandoned.

[51] Int. Cl.[7] .............................. C12N 5/00; C12N 1/00; C12C 1/00; A01N 1/02
[52] U.S. Cl. ......................... 435/392; 435/2; 435/297.1; 435/297.5; 435/305.1; 435/305.4; 435/309.2; 435/325; 435/366; 435/395; 435/401; 435/243
[58] Field of Search ................. 435/2, 297.1, 243, 435/297.5, 299.1, 299.2, 305.1, 305.4, 308.1, 309.2, 325, 366, 392, 395, 401, 287.9, 288.3

[56] References Cited

U.S. PATENT DOCUMENTS

| | | |
|---|---|---|
| 2,144,255 | 1/1939 | Carpenter . |
| 3,692,493 | 9/1972 | Terasaki . |
| 3,928,142 | 12/1975 | Smith . |
| 4,053,362 | 10/1977 | Sforza . |
| 4,187,861 | 2/1980 | Heffernan . |
| 4,282,317 | 8/1981 | Roth . |
| 4,421,849 | 12/1983 | Breuker . |
| 4,485,171 | 11/1984 | Ikeda . |
| 4,492,634 | 1/1985 | Villa-Real . |
| 4,678,753 | 7/1987 | Hempel et al. ................ 435/288.1 |
| 5,482,711 | 1/1996 | Medenica ..................... 424/195.1 |
| 5,827,681 | 10/1998 | Krug et al. ....................... 435/34 |

FOREIGN PATENT DOCUMENTS

| | | |
|---|---|---|
| 0239697 | 10/1986 | European Pat. Off. . |
| 0380768 | 7/1989 | European Pat. Off. . |
| 2639957 | 7/1988 | France . |
| 01174373 | 10/1989 | Japan . |
| 2263703A | 4/1993 | United Kingdom . |

OTHER PUBLICATIONS

Millar et al. Brit. J. Haematol. vol. 69 (2), pp. 197–203, abstract enclosed, 1988.
Goldberg et al. Am. J. Clin. Path. vol. 74 (6), pp. 771–775, abstract enclosed, 1980.

*Primary Examiner*—Leon B. Lankford, Jr.
*Assistant Examiner*—Christopher R. Tate
*Attorney, Agent, or Firm*—Stefan J. Kirchanski, Esq.; Graham & James LLP

[57] ABSTRACT

A patient replica is created from a layered culture medium where solid culture medium is formed so that a discontinuity exists between the layers. An infusion port is provided in registration with the discontinuity so that a fresh unadulterated sample of patient blood can be infused into the discontinuity to form a thin layer of blood between the layers of culture medium. The thin layer obviates the requirement for any anticoagulant allowing blood-borne pathogens to be readily cultured without using broth. Further antibiotics or other drug samples may be placed on the surface of the culture medium above the blood layer so that the antibiotic can diffuse through the culture medium and reveal the sensitivities of the cultured pathogens. Other samples of pathogens or tissues can be placed on the surface of the culture medium so that effects of drugs or growth factors present in the patient blood can be observed thereby allowing the entrapped blood layer to act as a biological replica of the patient.

32 Claims, 14 Drawing Sheets

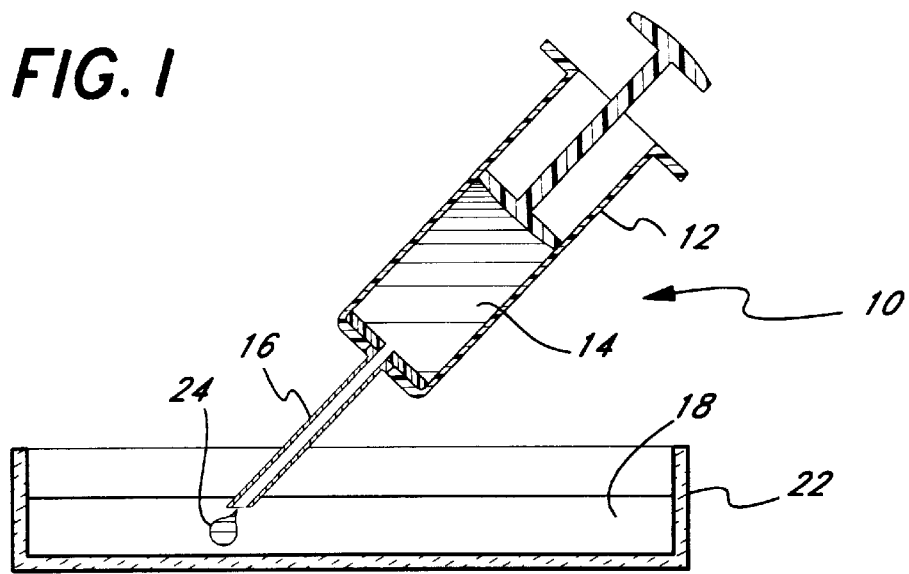
FIG. 1
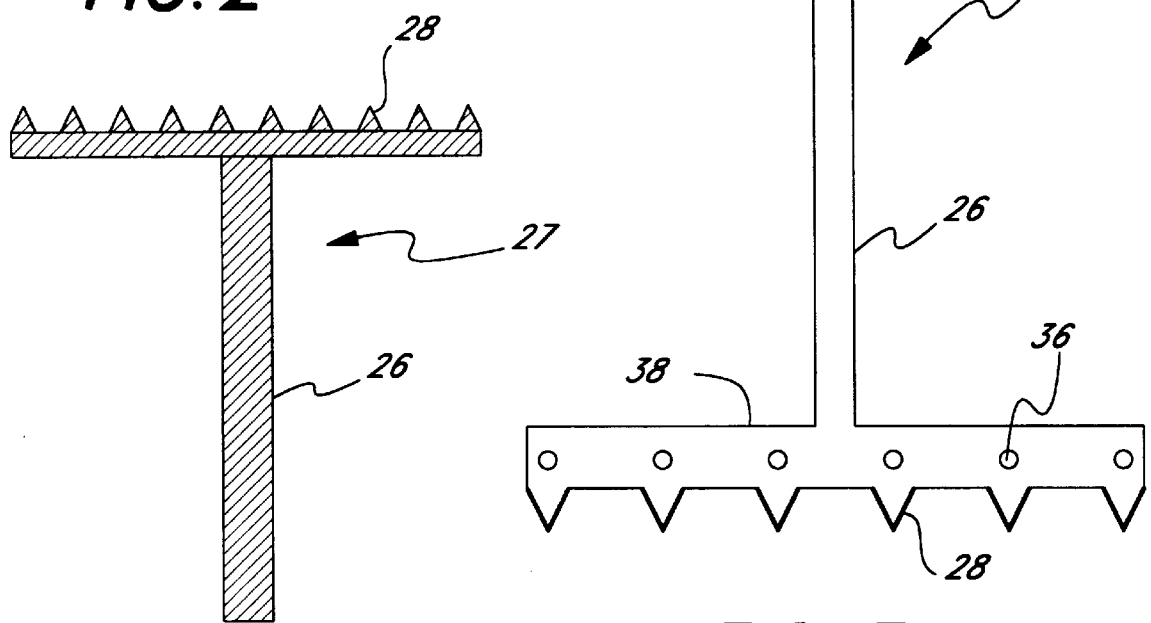
FIG. 2
FIG. 3

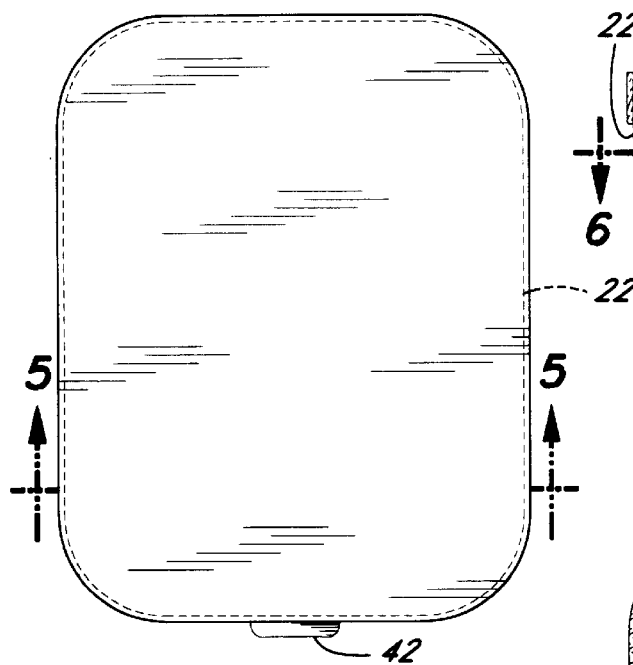
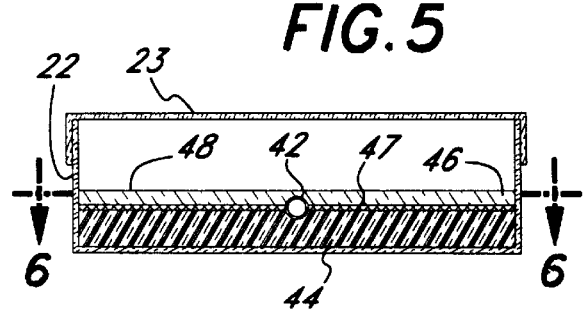
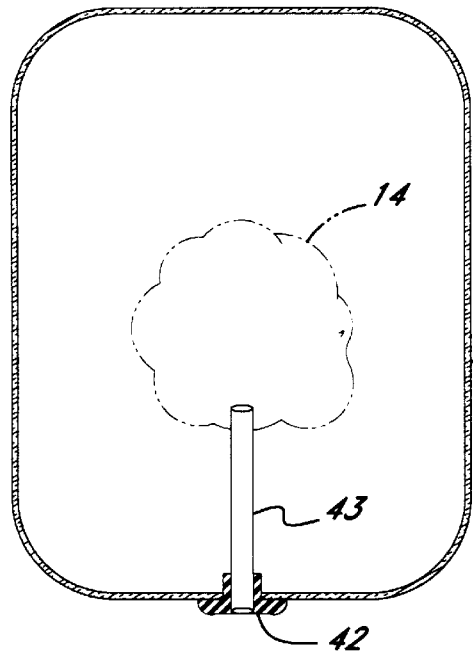
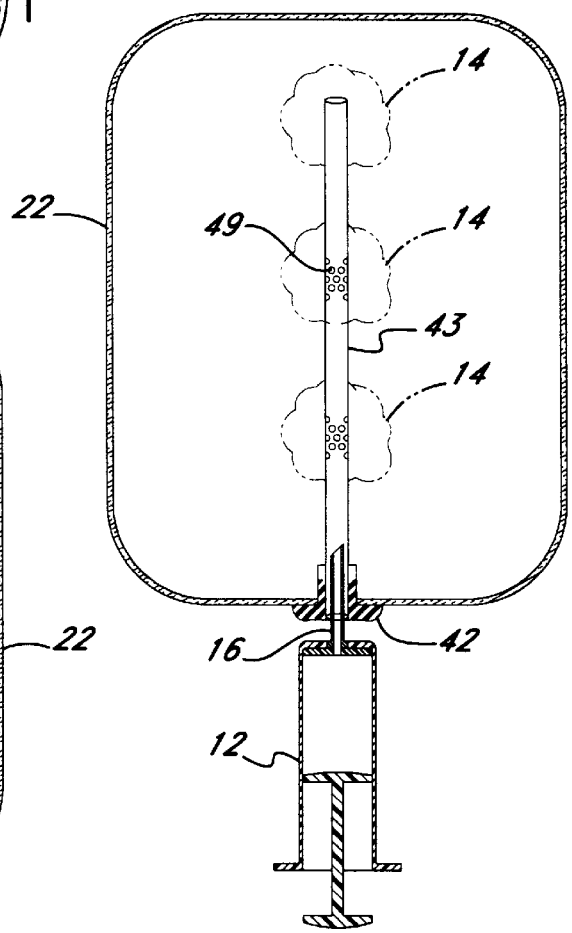

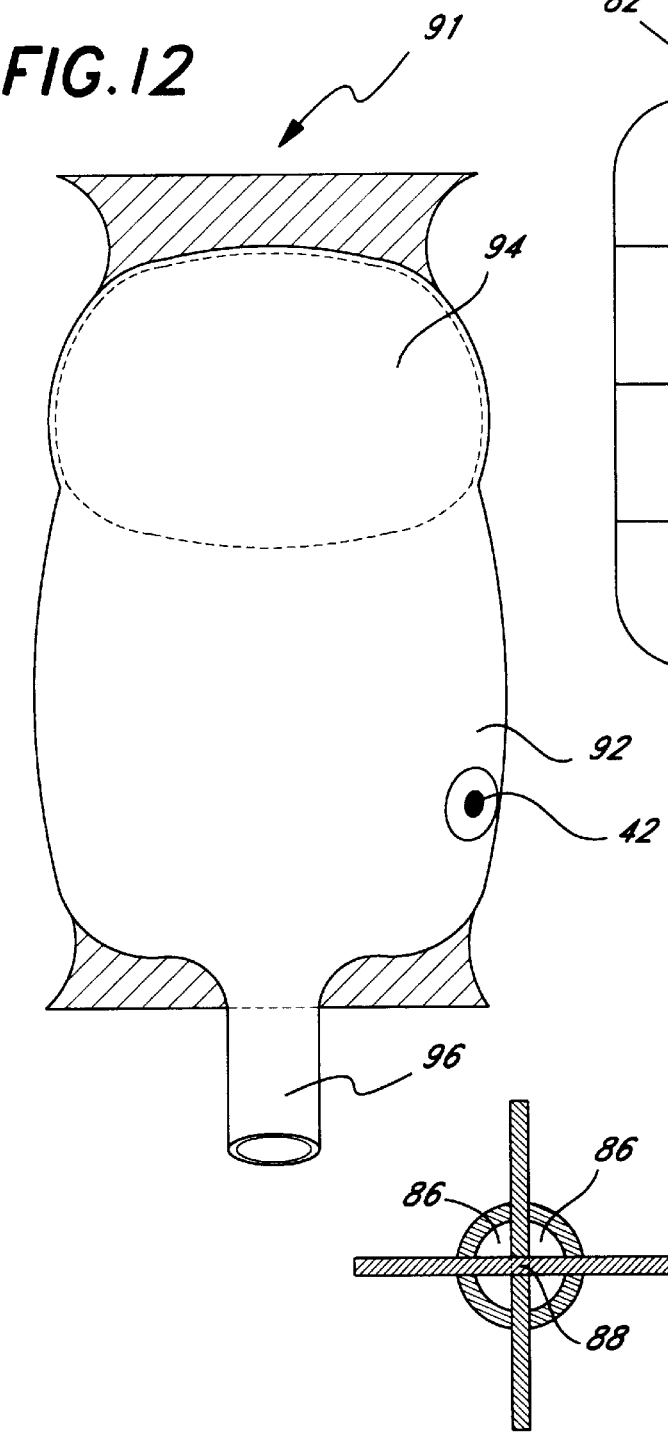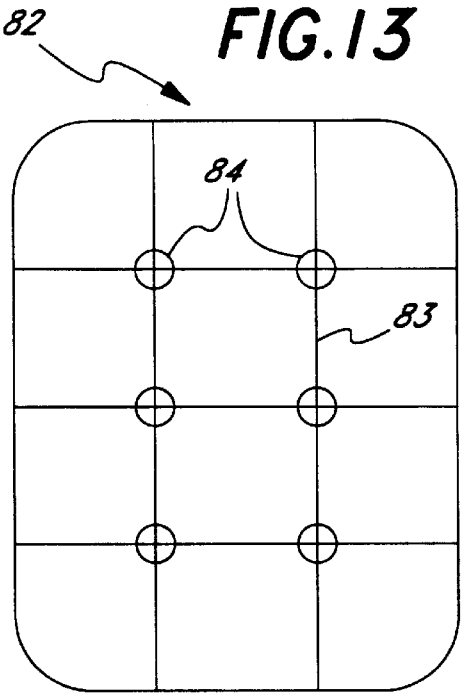

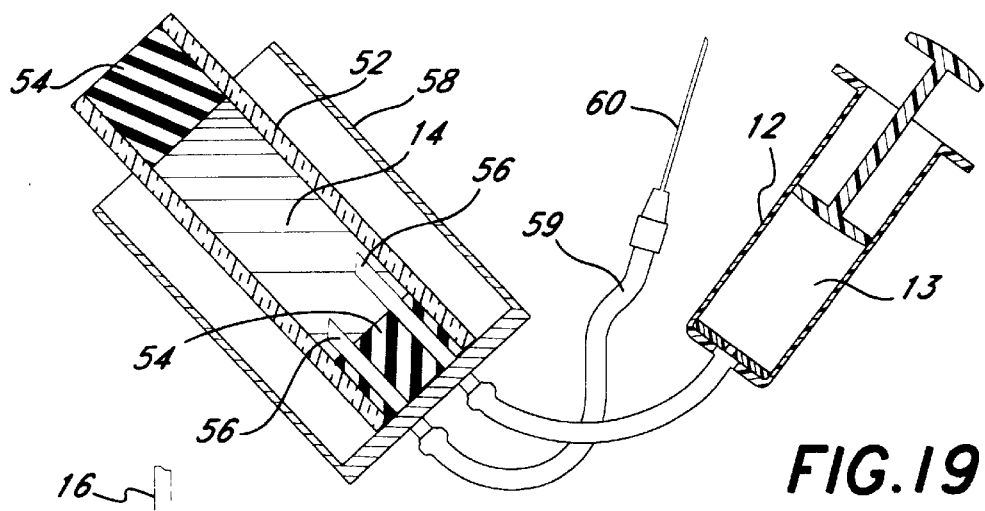
FIG. 19
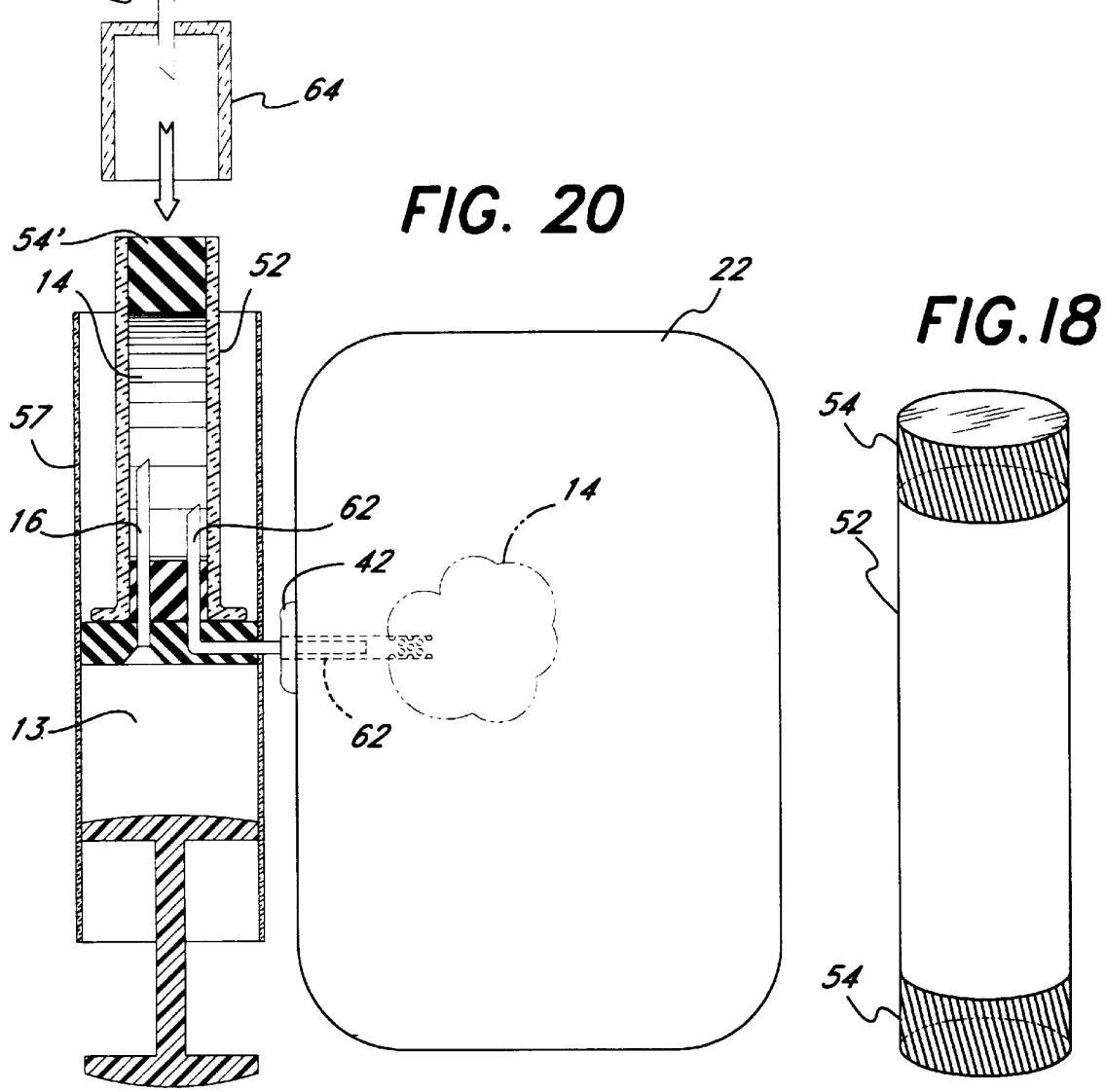
FIG. 20
FIG. 18

MICROPATHOLOGICAL PATIENT REPLICA BASED ON UNADULTERATED WHOLE BLOOD

The present application a continuation in part of application Ser. No. 08/826,429 filed on Mar. 20, 1997 now abandoned, which is incorporated herein by reference.

BACKGROUND OF THE INVENTION

1. Field of the Invention

The present is invention concerns the field of microbiological pathology and is more particularly addressed to a novel microbiological culture method and attendant apparatus that utilizes patient whole blood.

2. Description of Related Art

From the textbook of microbiology, *Biology of Microorganisms*, by Madigan, Martinko, and Parker, we learn that, "The most important activity of the microbiologist in medicine is to isolate and identify the agents that cause infectious disease." This is called the pure culture method of current practice, which proceeds by culturing a patient specimen or blood, thereby isolating and identifying pathogens, and using the resulting inoculum to make a pure culture, which may then be tested for sensitivity to antibiotics or other medications.

While much has been learned from this classic method, it has great limitations. The complex interrelationship of all the different microbes in a patient, with all the helpful and harmful elements in that host, are not considered as part of a whole. In research it is useful to study parts, but to treat an individual patient effectively, we must consider the whole person, at the time of inquiry. We must recognize that a human being is a mixed culture, and that pure cultures do not give physicians the information necessary to treat patients. This is vital at a time, as we are now experiencing, when pathogens are becoming resistant to antibiotics as well as more virulent.

This problem has long been recognized in microbiology, but broth cultures and mixed cultures were deemed too complex and too hard to work with. Agar culture media are difficult to use, and blood clots are difficult to deal with, so anticoagulants are routinely employed. Further, since labs are far distant, preservatives and refrigeration are necessary. Thus, artificial conditions, desire for convenience, and reliance upon pure cultures have left us less able to respond effectively to the pestilence of our times.

The process described herein considers the whole person, uses whole blood and specimen-not inoculum-and proceeds directly to the cure, not stopping to identify or isolate pathogens. The process is a basic simplification of microbiology/pathology (micropathology). Devices described herein allow the process to be used conveniently and protect personnel from potentially hazardous patient's blood. Availability of a process that can actually determine if a patient needs an antibiotic, and which one, may change the way antibiotics and other medications are prescribed.

The Problem

People become ill with pathogens, microbes such as bacteria, viruses, protozoa, fungi, yeasts, etc. Curative substances, e.g., chemical agents and antibiotics, penicillin for example, are used to inhibit the growth of, or kill, pathogen(s). Known sensitivity of a given pathogen to a specific antibiotic(s) allows the patient to be treated with that antibiotic, or combination, with a high probability of cure. The physician's dilemma is, how to determine which antibiotic or medication will be effective. But even before considering which antibiotic, the physician must determine if any antibiotic is indicated. Viruses and allergies can mimic bacterial infections but are not helped by antibiotics, which may actually worsen the condition. In addition, the unnecessary prescribing of antibiotics is part of the cause of pathogens developing resistance.

Currently, a patient with typical symptoms is treated with the antibiotic that has been effective in the past. However, many pathogens have become resistant to antibiotics which previously were effective. Because current art does not give the physician a practical means in the office to determine if an antibiotic is indicated, or which one of the many old or new antibiotics would be effective, the physician usually makes an educated guess and simply picks one, hoping it will help. The patient becomes the test of effectiveness. More and more often today, a previously effective antibiotic is ineffective for patients. Alternatively, the physician can take blood or a specimen from the patient-urine, feces, throat swab, sputum, cerebrospinal fluid, or pus-and send it to the lab for culture and determination of sensitivity of any discovered pathogens to antibiotics. Or, the physician can send the patient to a lab collection center for collection of an appropriate specimen.

Currently, laboratories are highly automated. Automatic technology and expert personnel are very expensive, resulting in one central lab with many peripheral collection centers. Consequently, the actual lab is often far distant from the physician or patient, requiring considerable time for specimens to be transported. Consequently, blood and specimens are usually refrigerated until they are received and tests have begun. Usually, additives to blood such as anticoagulants, preservatives, etc. are used as well. The distance of the lab does not allow freshly drawn unadulterated whole blood and fresh specimens at body temperature, natural human conditions, to be used in culture and sensitivity testing.

Currently, in the lab the specimen, other than blood, is placed in a sterile culture medium, usually agar in a dish, to grow the pathogen(s) causing the disease. Suspicious colonies of pathogens are identified and reported to the physician who can then prescribe medications based on known past sensitivity of that type of microbe. The study may be taken further. Colonies may be isolated and inoculum transferred to a sterile agar dish and recultured, then this pure culture tested for sensitivity to specific antibiotics. Unfortunately, the steps necessary to get a pure culture require considerable extra time.

When blood is cultured, liquid growth media, or broth, is used to permit complete mixing of the blood and medium. But the liquid state imposes its own limitations. The blood is mixed throughout the medium and is not contained within a space where pathogen colonies are more readily identifiable. Also, with broth there is no firm surface, as provided by agar, to streak with the patient's specimen. Also, if the specimen is added to broth and blood, some microbes may grow, but pathogens that need air for growth may be inhibited, and thus cannot not be discovered unless special steps are taken to aerate the broth. Also, most commercially available liquid blood culture media contain anticoagulants to prevent blood from clotting and clumping. Consequently, even if whole blood without anticoagulant were delivered to the lab, the culture medium would alter the natural state, defeating the attempt to create a surrogate host without artificial additives. The process of the present invention is not disturbed by natural clotting.

Currently, pathogens that are grown from broth are identified, isolated, and transferred to receptacles where colonies of microbes may be manipulated under controlled conditions, including testing for antibiotic sensitivity. Many steps and much time, labor, and expertise are required. Therefore, this method is little used except for the most critically ill, usually hospitalized, patients.

Currently, the process of mixing a patient's whole unadulterated blood with culture medium, such as agar, and adding a specimen, for growth of pathogens and antibiotic sensitivity, is not used. There are a number of factors mitigating against direct addition of blood to culture medium. Agar is difficult to work with; it either hardens or liquefies because of temperature changes. If heating is necessary, many pathogens in the blood are killed and cannot be discovered later. To make a pour plate to test sensitivity to antibiotics, inoculum is added to agar at 45+° C., the lowest temperature agar is liquid. That temperature is unnatural to the human body, thus many pathogens that thrive at normal body temperature, 35–37° C., are killed. Fragile anaerobic pathogens and some viruses, die upon contact with air. Other fragile microbes die when stained on a slide. Thus, current art is unable to readily culture and identify many fragile pathogens.

The handling of human blood is not without risk in this age of deadly pathogens such as hepatitis B, AIDS (HIV), and others. If the surface of agar were spread with a patient's specimen and the patient's blood were mixed with the agar using current means, e.g., a syringe/needle, personnel would be exposed to the risk of needle stick and the patient's pathogens. Devices are described herein that avoid or lessen that risk.

Currently, small paper discs which have been impregnated with different antibiotics, at various strengths, can be placed, one at a time by hand, upon the surface of agar where pathogens are growing. If the particular pathogen is sensitive to the antibiotic on the disc, a clear "zone of inhibition" will appear around the disc as the pathogen is killed or inhibited. This is not a practical method in the physician's office and, consequently, is little utilized at this time. In the lab, many discs can be placed on the surface of agar simultaneously by a special machine. But the lab is not where blood and specimens are fresh, and alive with microbes. Simple devices are described herein that simplify antibiotic testing in the physician's office where whole blood and specimens are fresh, allowing the culture of fragile organisms.

Disadvantages Of The Current Art (a) Current microbiological art does not give the physician a practical means to determine if an antibiotic is indicated and, if so, which one. Consequently, patients are being given antibiotics that were effective, often in the hope of curing an infection that proves to be viral or at least of inhibiting a possible secondary bacterial infection. However, indiscriminate use of antibiotics and similar drugs is causing patients to become allergic to these drugs while the microbes become resistant. There are two dangerous consequences: the patient will not be cured of infection; and the patient becomes a host who may unknowingly be a carrier and transmit resistant pathogens. The process of using naturally augmented media to make a patient replica allows determination of the correct drug to use (i.e., antibiotic sensitivity) for individual patients because factors, both known and unknown in the patient's blood that will affect how a pathogen responds to a given antibiotic are automatically considered in this novel process of determining antibiotic sensitivity.

(b) A patient's unadulterated whole blood is difficult to work with since it coagulates and decomposes quickly. Consequently additives, e.g., anticoagulants and preservatives, and refrigeration are currently used, but this alters the natural state of the blood and limits what may be cultured from it. The process herein described, with accompanying devices, does not have this disadvantage.

(c) Specimens are routinely transported to laboratories for analysis but many pathogens are fragile and do not survive the trip. Samples are picked up from the physician's office and transported to the lab in sterile containers but not under natural conditions. Much time may elapse before the culture process is begun. Pathogens which are not vigorous enough to survive and replicate under these abnormal conditions cannot be identified.

(d) Many pathogens do not grow in culture media now in regular use. For example, sheep blood which has been heated to release iron is mixed with culture media, referred to as chocolate agar, to facilitate growth of certain pathogens. Sterility can be maintained. However, sterile killed sheep's blood does not replicate freshly drawn unadulterated whole human blood at body temperature, especially all the different elements in a specific patient's blood at the time the patient is experiencing a particular illness.

Also, liquid growth media, broth, normally has anticoagulant added, thereby altering the complex natural state of the blood. It is known that anticoagulant kills a certain percentage of some microbes in the broth. Thus, current broth methods may prevent blood culturing of fastidious organisms.

Other types of agar also use blood as one of their component. However, the blood is not the patient's blood, does not contain all natural elements, has been heated and is sterile, and thus cannot be a replica of that specific patient at that specific time of illness. Standard pour plate method adds inoculum to 45+° C. agar, thereby killing many fragile microbes that cannot survive outside the range of body temperature, 35–40.5° C. If the patient's blood is heated above about 40.5° C., the blood begins to decompose, also becoming sterile, thus defeating the attempt to culture pathogens.

(e) Pathogens that grow in the lab do not always respond the same in the patient as general experience of the past indicates. As noted above, an ill patient has a unique mix of elements, most unknown to the physician. An antibiotic that may be effective in most people may not be effective in others and current art does not offer a way to determine this, except by using the patient. But, the patients who are most needy of immediately effective antibiotics are least able to withstand this process of experimentation.

(f) Even when successful, current art of pure culture, i.e., specific identification and isolation, requires much time to determine which antibiotic will be effective. For a few patients, a day saved may be a life saved. For many with chronic illnesses, such as AIDS, morbidity can be reduced by effective treatment of a secondary infection. For all, a day earlier institution of an effective antibiotic or medication is a day their illness does not worsen; hospitalization with its attendant costs and risks may be avoided. At the very least, patients can resume their active lives earlier, including going back to work. Delay in effective treatment is very expensive, both individually and nationally.

(g) Currently, many patients are tested after they are already taking antibiotics, medications, etc. This is considered to be a problem because the currently taken medications may suppress the pathogens and make them difficult or impossible to isolate in pure culture. With the process and devices described herein the patient's current natural state is desired, including any medications taken. Obtaining pure cultures is no longer an essential goal; however, traditional identification and sensitivity testing may still be done in two steps using the present invention.

(h) Currently, when tumors are removed from the body, they are usually adulterated in some way before they are examined or cultured, e.g., freezing, refrigerating, preservative solutions, etc. Consequently, tests of the tumor cells or the patient's cells or other factors are inaccurate or incomplete. The process and devices described herein use specimens in the natural state and under natural conditions, thus eliminating these limitations. For example, a bag-in-a-bag device can be used as a transport apparatus to convey tumors to the lab under natural conditions, using the patient's blood. Also the research process in the cancer lab may start in the bag with additives, such as collagenase, to separate cancer cells. Such a device allows every cancer patient to have access to the expertise of a cancer research center even though that center may be remote.

(i) There is risk of life-threatening contamination to medical or lab staff who handle human blood, particularly when needles are used. Using current art, the results obtained from the process of this application would tend to only be the product of experts in laboratories, not of physicians in their offices where blood and specimens are fresh, unadulterated, whole, and at body temperature. Without the present invention these results, so valuable in an era of increasingly resistant and virulent pathogens, would be unobtainable.

(j) Placing antibiotic discs on culture media one at a time by hand is time and labor consuming, while increasing the risk of contamination, so the physician almost always uses the lab for antibiotic sensitivity testing. Thus, current methods limit the physician to use of a lab, even though ideal conditions of blood and specimen are available in his/her office.

(k) All antibiotics and medications are not readily available on discs, and even when so, are relatively expensive. A device described herein can use pills, capsules, or liquid to test sensitivity.

DEFINITIONS GERMANE TO THIS APPLICATION

Culture Medium-a medium for growing living organisms, e.g., human cells or microbes such as bacteria, viruses, etc., which provides the requirements for growth. Substances may be added to solidify the medium, or to enhance or to inhibit growth, or for any other purpose. Typically culture medium will be solidified agar (agarose) to which various nutrients and growth factors have been added. Any other type of support media such as gelatin, acrylamide, cellulose, carbohydrate gums, etc. can also be used.

Whole Blood-blood in the natural state, containing all helpful and harmful elements, whether known or unknown, such as clotting factors, pathogens, antibodies, etc.

Replica-an exact model of an original in all important aspects.

Micropathological Replica-a culture medium containing a patient's blood, including all the elements naturally present in that person's blood, maintained to natural human standards, aseptically, providing a laboratory model for study; in the present invention a micropathological patient replica is formed by using whole patient blood to act as a surrogate for the various growth factors, nutrients, pathogens, and other elements, that are present in the patient being replicated.

Additives To Blood-anticoagulants, preservatives, and other substances added to blood taken from a patient to render that blood stable for later analysis or treatment.

Anticoagulant-a substance that prevents blood from clotting, such as heparin, oxalate, citrate, ethylene diamine tetraacetic acid (EDTA) or sodium polyanetholsulfonate (SPS).

Aseptic-sterile conditions, e.g., conditions in which no foreign organisms such as bacteria are added.

Specimen-any sample of body tissue except blood, e.g., urine, feces, throat swab, sputum, cerebrospinal fluid, pus, cancer cells, etc.; for clarity in this patent application, blood is specifically distinguished from specimen.

Inoculum-microbes that are grown from a specimen or patient blood (i.e., that were originally present in the specimen or blood), that are identified and isolated, using the current methods of microbiology, or the patient replica process of the present invention.

Pathogens-microbes such as bacteria, viruses, protozoa, fungi, yeasts, etc. that cause disease.

Resistance-the ability of a pathogen to change so it is no longer vulnerable to a particular antibiotic(s) or similar anti-infective agent.

Pour plate-a culture dish where agar culture media (or similar solidifiable media) and inoculum have been mixed, typically at 45° C. or above.

Microbe-a microscopic organism, generally pathogenic in the context of the present invention, including bacteria, fungi, protozoans and viruses.

OBJECTS AND SUMMARY OF THE INVENTION

One object of the present invention is to provide an improved way to grow microbes directly from a patient's blood, with or without an additional specimen, thereby determining if a medication, e.g., antibiotic, is indicated, and when indicated, to determine which antibiotic(s) will be effective for a particular patient at a particular time with greater speed and sensitivity than the current art;

Another object of the present invention is to test medications, antibiotics, etc. to determine the smallest effective dose for a particular patient by allowing the specific chemistry of the particular patient, as typified by the patient's own blood, to influence the test or to test medications, antibiotics, etc. to determine a standard dose for general use by averaging the results of a plurality of patients;

It is still another object of the present invention to grow cancer cells, and/or white blood cells, etc. as influenced by the patient's own individual chemistry by using cells from a patient's tumor or blood, for a variety of purposes. For example, the cancer cells can be used to treat cancer by using the patient replica to determine that patient's response to treatment, or to create a vaccine; and It is a further object to diagnose or treat any disease, e.g., AIDS or Epstein-Barr, or to determine the stage of an illness, to determine the status of a patient during the course of an illness, or for other related purposes.

These and further objects are met by a layered culture medium where solid culture medium is formed so that a discontinuity exists between the layers. An infusion port is provided in registration with the discontinuity so that a fresh unadulterated sample of patient blood can be infused into the discontinuity to form a thin layer of blood between the layers of culture medium. The thin blood layer obviates the requirement for any anticoagulant allowing blood-borne pathogens to be readily cultured without using broth. Further, antibiotics or other drug samples may be placed on the surface of the culture medium above the blood layer so that the antibiotic can diffuse through the culture medium and reveal the sensitivities of the blood-borne pathogens. Other samples of pathogens or tissues can be placed on the surface of the culture medium. A method to refresh a layer with a periodic infusion of serum, thereby replicating a portion of the lymphatic system, is also described. The result is that the effects of drugs or growth factors present in the patient's blood can be observed, thereby allowing the entrapped blood layer/growth medium/serum layer/ specimen to act as a biological replica of the patient. Material diffusing from the surrounding culture material potentiate the growth of microbes within the blood layer for ready detection of blood-borne disease. Simultaneously, factors diffusing from the blood can influence the growth of cells or microbes on a surface of the culture medium which is free of direct contact with the blood.

The present invention fills the long-felt need of a having an in vitro laboratory test that accurately reflects the conditions in a particular patient. Accordingly, antibiotic determination using this invention provides more information, more rapidly. Not only are sensitivity and resistance apparent, but some microbes have actually learned to thrive in the presence of some antibiotics, probably because the antibiotic suppresses other harmless microbes that compete with the given pathogenic microbe. This effect which can only be seen in the mixed culture conditions provided by the present invention places the patient at tremendous risk since the "therapy" actually encourages the pathogen.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings where like structures are indicated by like signs.

FIG. 1 shows a syringe with needle used to inject a patient's blood into the culture medium showing a drop of said blood embedded within the medium;

FIG. 2 shows a rake for breaking the surface of gel culture media to mix blood, specimen, or other substance into said culture media;

FIG. 3 shows a hollow rake that is connected to a blood transport device (such as those shown in FIGS. 8–10), or attached to a needle-syringe or to a syringe;

FIG. 4 shows a top view of a rectangular culture dish with round corners, equipped with means to infuse blood into the dish;

FIG. 5 shows a side view of the dish of FIG. 4 equipped with a loose fitting lid;

FIG. 6 depicts a top view of a dish with layered culture medium wherein a tube conducts blood into the dish to disperse it between the layers thereof;

FIG. 7 is a top view of a dish showing a needle-syringe injecting blood into an extended tube constructed with a plurality of holes to direct blood between the layers of culture media;

FIG. 12 shows a bag-in-a-bag device for use with the process of the present invention;

FIG. 13 shows a grid made to fit the layered culture dish of the present invention and intended to place a plurality of antibiotic impregnated discs or other drug samples at regular intervals on the medium surface FIG. 14 shows the grid-disc holder of FIG. 13 in greater detail;

FIG. 15 is a side view of the disc holder of FIG. 14 showing a sharp point projecting below the center of each held disc into the culture media, thereby allowing sub-surface blood to contact each antibiotic sample;

FIG. 18 shows a tube with rubber stoppers at either end for use with the present invention;

FIG. 19 is the similar to the device shown in FIG. 10 except the double-stoppered blood-drawing tube of FIG. 18 is used;

FIG. 20 shows a device similar to that shown in FIG. 11 with the addition of a double-stoppered tube and a vacuum tube blood drawing device;

DETAILED DESCRIPTION OF THE PREFERRED EMBODIMENTS

Figure 8:
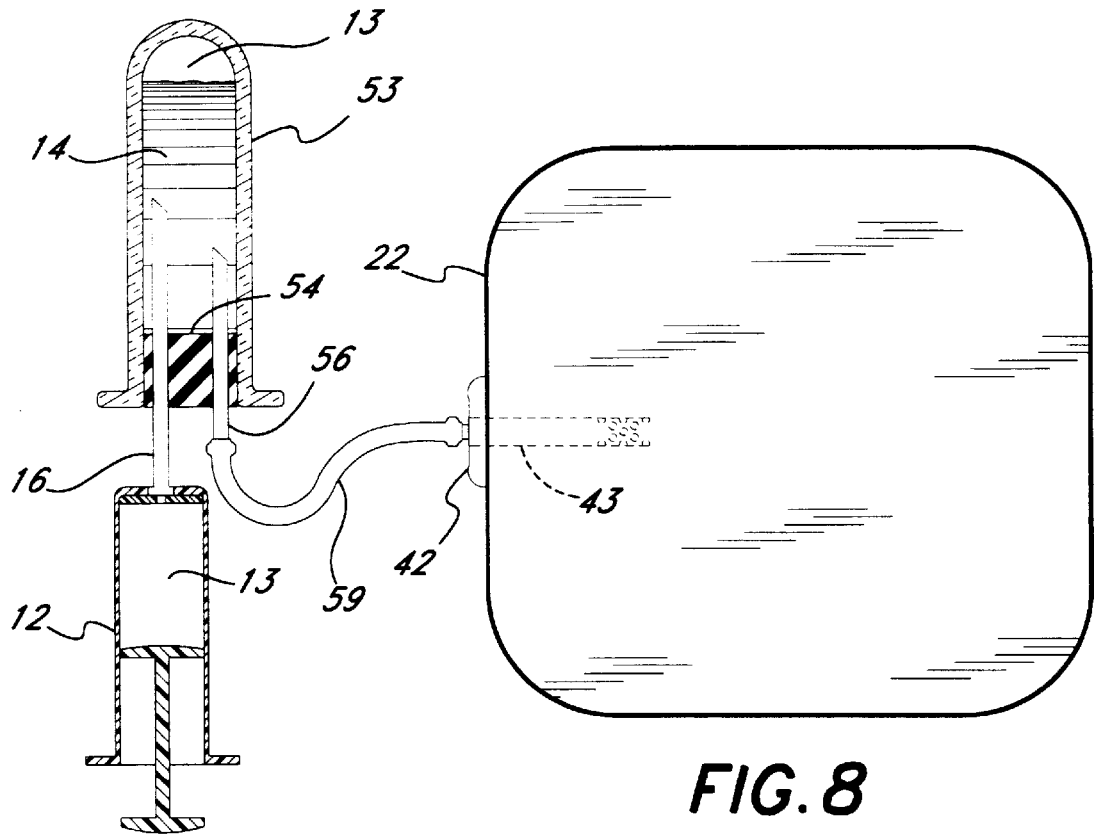
FIG. 8 shows a device for transporting patient blood for use in the layered culture medium of FIG. 6.

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein specifically to provide an improved culture method and associated devices for readily culturing pathogens or cells from unadulterated whole blood between layers of solid culture medium. For example, a bag-in-a-bag device can be used to transport and process tumor specimens for the cancer research lab, where the layered device is then used to grow patient's cancer cells with the media enriched by the patient's blood, thereby providing a micropathological patient replica. Similarly, the devices can be used to culture or activate a patient's leukocytes or can be used to transport patient blood to a laboratory.

CREATION OF A PATIENT REPLICA

The basic process described herein is the creation of a laboratory patient replica by using the patient's freshly drawn unadulterated whole blood as a component of a culture medium, thus providing all clotting factors, microbes, antibodies, pH and beneficial or harmful elements that actually exist in the particular patient. The patient replica may be used for a variety of purposes, such as growing cancer cells for creating a vaccine against that cancer, or for determining other information about the cancer. The replica is also useful for growing microbes from a patient's specimen and determining the microbes' sensitivity to a curative agent such as an antibiotic. Other possible uses of the patient replica are to diagnosis an illness, to treat an illness, to determine the stage of an illness, to determine the status of a patient during the course of an illness or during the course of therapy, etc.

For example, whole blood from a patient, freshly drawn, at body temperature, unadulterated, e.g., without additive such as anticoagulant or preservative, etc. is aseptically added to culture media before the blood decomposes. This mixture is then incubated at body temperature, 35 to 37° C. preferred. In addition, specimen from the patient may, or may not, be used. The mixture may be refreshed periodically with the patient's serum. Organisms which grow in this natural mix and temperature, whether from blood or specimen, can then be tested, by any means, for any purpose. Thus, it can be determined that an antibiotic will not be effective. Alternatively, an antibiotic can be determined to be effective in an individual patient's unique mix of biological elements, at a particular time. This avoids the all too common problem where a particular antibiotic is effective against a pure culture of a pathogen but is ineffective in a given patient because of some peculiarity of the patient's individual chemistry. Also, patients do not contain pure cultures. The goal is to test drug sensitivity against the background of the patient's chemistry and with the interactions of all of the variety of benign and harmful microbes that may exist within the patient.

According to the present art when a specimen is tested for pathogens, lab technicians determine which type of pathogen is grown from the specimen and then report it. Physicians assume drugs that killed this particular type of pathogen before will kill it again. Resistant pathogens defeat this system. Studies which proceed to isolate a pure culture of pathogens from inoculum and then test the pure culture for drug sensitivity take more time. The process described herein proceeds directly to cure, neither isolating nor identifying the pathogen but only identifying what will kill it. The process promoting the use of a mixed culture in this way represents a new approach in microbiology. Nevertheless, for research purposes, pathogens can also be identified and sensitivities tested in the conventional manner by subculturing them from the patient replica of the present invention.

As discussed above, it is well known that patient's whole blood often contains pathogens that may be multiplying in the blood or being swept into the circulating blood from some focus of infection. Therefore, whole blood is often cultured in an attempt to isolate these pathogens. Further, whole blood contains quantities of any drugs being administered to the patient as well as a whole host of natural growth factors and other substances that constitute the unique biochemical profile of the patient. In this process these factors are available for determining the existence of pathogens and their drug sensitivities. Traditional methods of culturing pathogens from blood rely on a liquid broth culture. This requires the addition of anticoagulants to avoid clot formation within the broth. Also, since the whole blood is diluted into the broth, delicate pathogens may be killed or inhibited. The use of preservatives and refrigeration can further skew the results. Also, there is no convenient way that natural patient factors present in the whole blood can be utilized to affect the growth of pathogens from a patient specimen. A first goal of the present invention is to allow culture of pathogens from unadulterated whole blood. A second goal is to allow factors present in the unadulterated whole blood to affect the culture of pathogens from a patient specimen. A third goal is in cancer therapy/research where the invention is used to transport tumor specimens and patient blood to the laboratory where the invention is used to grow cancer cells and/or white blood cells using the layered culture dishes.

The simplest device to accomplish the first goal is a receptacle, such as a dish, into which freshly drawn unadulterated whole blood is mixed with a culture media, with or without additives (not shown). The culture media may be of any kind, e.g., powder or granules to mix with an aqueous solution. The resultant mixture may then be used as a single layer, or the mixture may be poured into a receptacle, such as a culture dish, upon an already poured layer of culture media. A patient specimen may or may not be added, to the top of the first layer, between the first and second layer, or into the mixture.

A problem is that gel agar, the most common culture medium, resists mixing so that it is very difficult to directly mix the whole blood into normal medium. If the agar is melted by heating, there is significant danger that delicate pathogens will be damaged or killed. Therefore, it is necessary to have some sort of instrument or device to help mix the agar with the medium. An example of such an instrument is a needle-syringe combination that may have been used to actually draw the blood from the patient. As shown in FIG. 1, the needle-syringe 10 can simply inject small drops of blood into the surface of the agar. In FIG. 1, blood 14 in a syringe 12 is injected through a needle 16 into a solid culture medium 18 contained within a dish 22, thereby depositing drops 24 of blood which can then be mixed into the agar with the same needle 16. The advantage of this approach is that because the blood is distributed into the medium, it is possible to dispense with anticoagulants which are known to alter and often inhibit the growth of pathogens. That is, the distributed blood is unable to form into significant clots (e.g., large clots in which there is separation between clot and serum). However, the total amount of blood readily introduced in this way is relatively small. Other approaches are necessary if larger total amounts of blood are to be used. Clearly, if the pathogens being sought are present at a low concentration, the larger the amount of blood used, the larger the chances of finding the pathogen.

FIG. 2 shows a miniature rake 27 with a handle 26 and tines 28, that will break the gel and mix the blood, applied by any convenient means. The rake can be made from any material that is readily sterilized. However, the tines 28 should be sufficiently blunt to avoid accidental puncturing of the skin. For safety as well as economy it is prudent to make the rake 27 out of some sort of soft plastic/elastic material such as polyurethane although other materials such as glass or metal can also be used. Another example is a hollow rake 32, FIG. 3, that combines two functions, i.e., breaking the gel while simultaneously dispensing the blood which is to be mixed into the gel. This hollow rake 32 may be directly attached by a connector 34 at an end of the handle 26, to a needle-syringe combination, to a syringe, or to a thin tube as shown in other drawings herein. A valve may optionally be used to control flow. Thus, blood is forced through the hollow handle 26 and flows out of openings 36 in transverse member 38 and is mixed by the blunt tines 28. This rake offers not only simplicity and convenience but is safer for blood handlers than needles and their attendant danger of needle sticks.

Although the just-described rakes can be used to distribute blood into a semi-solid culture medium, the blood may not be evenly distributed leaving the possibility of clot formation. The preferred way of distributing the unadulterated blood is through the use of a layered culture dish as shown in FIGS. 4–6. In FIG. 4, a dish 22, with or without a lid 23 is constructed with a port 42 to direct blood through one, or more, sides(s) and between layers of culture media therein. A rectangular dish with round corners is preferred since the dishes can be more effectively packed together and offer increased surface area for growth of microbes, but a standard round petri dish or any other shape with or without round comers will work. This culture dish may be used in a number of different ways.

EXAMPLE 1
Using A Layered Culture Dish

In FIG. 5, solidifiable culture media, such as agar, generally with those additives necessary for growth of pathogens, is poured into a dish 22 and then cooled to become a layer of gel 44. Then an additional layer of culture media is poured upon the first layer, making a second layer of culture media 46, and cooled to the gel state. Thus prepared, the two layers of culture media do not bond, thereby creating a potential space or discontinuity 47 between them. The dish 22, now containing two layers of culture media, may be stored until needed. When the unadulterated blood sample is injected through the port 42, it spreads into an even blood layer sandwiched between the two layers 44, 46 of media. Although micro-clots may appear because the blood layer is thin and even, large clots do not form. Because of the intimate contact with the culture media any microbes within the blood are provided with an excellent milieu within which to grow while leaving an upper surface 48 blood-free. Colonies of pathogens are readily observable in the thin blood layer or slides may be made and stained to enhance visibility of the pathogens. Further, growth factors or inhibitors, etc. within the patient's blood sample diffuse into the culture media and may affect growth of organisms placed in contact with the media. For this reason the second layer 46 is preferentially quite thin to maximize the rate of such diffusion. Although the upper layer 46 has been referred to as being "poured," it could also be sprayed on or placed on as a membrane or a layer of plasmoid mesh which is currently used to treat burns. The layered structure allows the upper surface 48 to remain blood-free, thus the upper surface 48 of the culture media may be streaked with a patient's specimen, sputum, etc. with no danger of any microbes growing there having come from the patient blood. A blood-free surface may also be obtained by turning a dish upside down to release the culture medium which provides the untouched bottom of the medium as a blood-free surface. Alternatively, a patient specimen may not be used, the study focusing upon the patient's blood, only. FIG. 6 shows the layered dish 22 in which the injection port 42 is equipped with a short distribution tube 43 to further distribute the blood 14 between the layers, or to distribute fresh serum periodically.

To recapitulate use of the layered culture dish, blood is drawn from the patient and, without additives, is immediately transferred, aseptically, by any means, to the infusion port 42 disposed on the dish 22. The infusion port 22 may or may not be equipped with a valve to prevent back flow of the blood sample. Examples of devices that may be used to transfer blood are shown in FIGS. 7–11. In FIG. 7 the injection port 42 is equipped with a relatively long distribution tube 43 (as compared to FIG. 6) which has a plurality of distribution holes 49 for spreading the blood 14 between the layers. The patient's blood is transferred by such a device into the dish 22 through one, or more, side(s) thereof and infused into the potential space 47 formed from a discontinuity between the layers of culture media therein, thus separating the layers. The layered media can be stored in advance in an incubator at body temperature so that there will no temperature shock to fragile pathogens when a blood sample is introduced into the dish. The result is a layer of whole blood at body temperature between two layers of culture media, with or without specimen placed on the blood-free surface 48 of the upper layer 46. It is important that patient blood not leak along the lateral walls of the dish and thus reach the upper surface 48. Such leakage can be prevented by special structures discussed below or by use of media formulae or precoatings on the dish which enhance binding of the culture media to the dish. As is well understood by any of skill in the art, the dish 22 should be closed by a lid 23 to preserve sterility. Preferably the lid 23 is optically clear to permit observation of pathogen growth. There is considerable advantage to "locking" the lid 23 in position with a gasket, O-ring, adhesive or other fastening means. This prevents inadvertent opening of the dish 22 and also allows the device to be air tight as for culture of anaerobic organisms. For aerobic culture a filter allowing air and not microbes to pass, is installed in the lid. Also, the dish 22 can be made quite large to accept a relatively large blood sample and permit multiple simultaneous tests as in a research setting. Also, the dish may have a lid, FIG. 35, with a plurality of injection ports which facilitate manual or automated application of drugs for testing.

The resultant dish with blood layer/mixture is incubated at body temperature, about 35–37° C., at which temperature some of the blood factors will diffuse into both layers of culture media. Viable pathogens, whether from specimen or blood, will grow upon, or in, this blood-culture media melange. Antibiotic sensitivity may be tested directly by placing antibiotic samples on the surface 48, thereby providing a test of antibiotic sensitivity upon a replica of the actual patient, either in the standard two steps of identification and sensitivity testing or in a single step using a mixed culture. Also, serum may be periodically infused. The system is considered a replica because it contains growth factors and inhibitors from the patient's blood that are indicative of the unique biochemical status of that particular patient.

Figure 9:
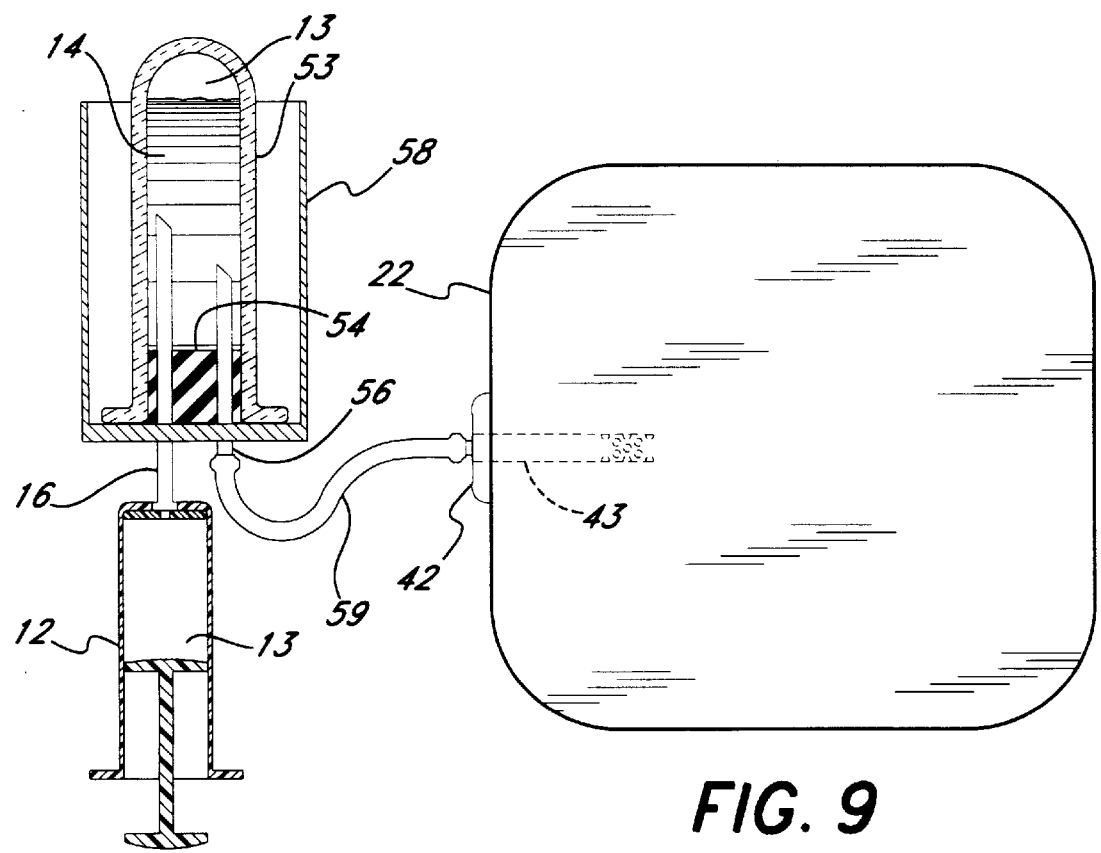
FIG. 9 shows a variation of the device of FIG. 8.
Figure 10:
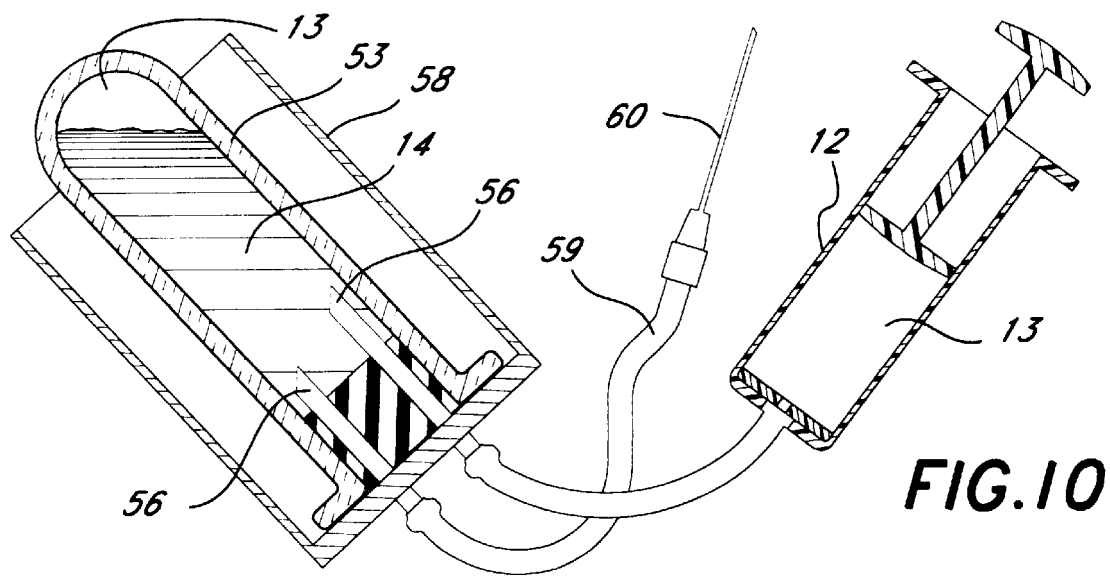
FIG. 10 shows another device for carrying patient blood for use in the layered culture medium of FIG. 6.
Figure 11:
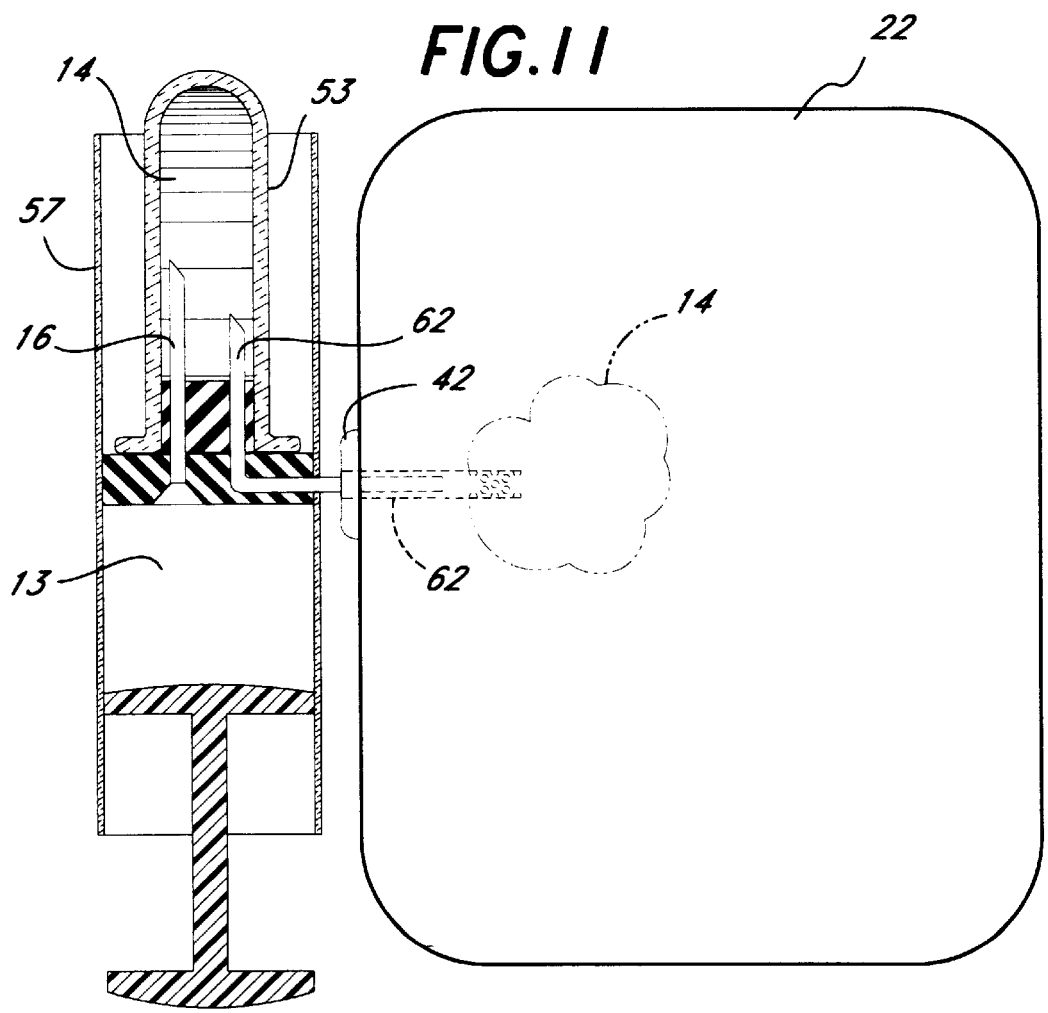
FIG. 11 shows yet another blood transport device configured so as to be directly linkable to the layered culture media of the present invention.

In FIG. 8 a typical vacuum tube 53 filled with blood 14 is used to deliver freshly-drawn blood into the layered culture dish 22. A flexible delivery tube 59 is attached to the infusion port 42 and the blood tube 53 by means of a needle 56 inserted through the stopper (serum cap) 54 of the blood tube 53. A syringe 12 with an attached needle 16 is used to inject air 13 into the inverted blood tube 53, thereby driving the blood 14 through the delivery tube 59 and between the layers of culture media in the dish 22. FIG. 9 shows an essentially similar arrangement except that a special holding tube 58 that comes ready equipped with needles 16, and 56 (and optionally the delivery tube 59) is used. In this arrangement the syringe (and the delivery tube 59, if not already attached) is attached to the holding tube 58 and then the blood tube 53 is inserted into the holding tube 58 and pressed down onto the needles 16, 56 so that they penetrate the stopper 54. This arrangement makes it impossible for personnel to accidentally stick themselves with the needles since the needles are completely enclosed by the holding tube 58. FIG. 10 shows a similar arrangement where the delivery tube 59 is equipped with a blunt needle 60 which is ideal for injection of blood through the infusion port 42. The blunt needle 60 is incapable of causing a needle stick (i.e., of penetrating human skin) so it is safe to use. FIG. 11 shows a special combination syringe/holding tube 57 equipped with a blunt right angle needle 62 designed for insertion into the infusion port 42.

Figure 36:
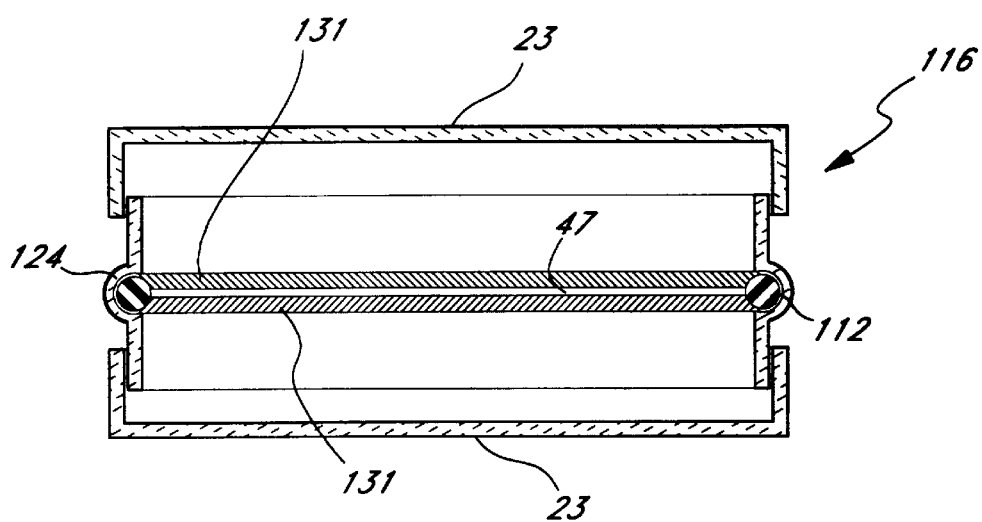
FIG. 36 shows a cross section of a dish-type device of the present invention that has two lids and an inner groove 124 on a side wall to accept a ring that holds two layers of membrane with a means to infuse liquid into the sealed space between the membranes.

There are many possible variations. The second layer of culture media may be made of a different material than the first layer. The two layers can be different types of growth media with the lower layer 44 containing ingredients especially conducive to the growth of blood-borne pathogens while the upper layer 46 contains nutrients conducive to the growth of pathogens suspected to be in the patient's specimen which is subsequently placed on the upper surface 48. To promote separation of layers or adherence to the sides of the dish, the proportion of gel-forming agent (e.g., agar) to culture media may be increased and/or other additives may be used. Membranes may be used. Double membranes in a "dish" with two lids FIG. 36 allow blood to be infused between the membranes and both outer surfaces of the membranes available for application of specimen or cancer cells, and the culture refreshed with serum on the other surface, or other purpose.

EXAMPLE 2
Method of Producing Non-Adhering Layers

As explained previously, if a first layer of melted media (e.g. agar) is poured and allowed to gel, a second layer subsequently poured on top of that layer will generally not adhere to it. However, there are several strategies to ensure non-adherence of the layers; the following is a description of one way of constructing a working two-layer culture dish of the present invention. The first step is to bore a hole in the side of a 150 mm plastic petri dish to act as an infusion port. This hole is then plugged with a suitably sized piece of rubber septum or rubber stopper. Under sterile conditions 60 ml of Mueler Hinton (or other suitable nutrient medium) is poured into the dish and allowed to gel.

Figure 24:
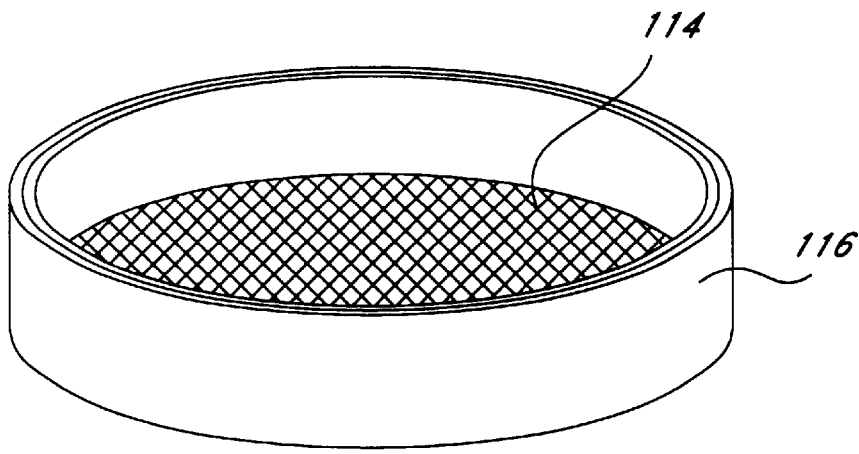
FIG. 24 shows a hoop or double hoop with its bottom covered with a mesh so that culture medium can be poured on top.

Next (see FIG. 24) a tightly fitting double hoop 116, rather like an embroidery hoop, is constructed to fit tightly into the modified dish. One method of forming each of the two hoops is to join the ends of suitably sized polycarbonate strips with a solvent cement such as PS Weld-On 3. One side of the hoops may be notched to fit over the infusion port (not shown). Formaldehyde-free nylon netting ($\frac{1}{8}^{th}$ inch mesh) is stretched tautly in a large embroidery hoop. The stretched netting is then trapped between the double hoops described above and a razor blade or similar implement is used to trim the double hoop with its enclosed netting yielding the structure shown in FIG. 24. The hoops 116 and enclosed netting 114 are sterilized by commonly employed methods such as radiation or ethylene oxide. The hoops, netting side down, are placed in a suitably sized sterile petri dish and approximately 45 ml of sterile Mueler Hinton agar (at about 48° C.) is poured into the hoops and allowed to harden. Then the hoop assembly including a layer of agar is placed on top of the layer of agar in the first dish (with the notch accommodating the infusion port).

Figure 25:
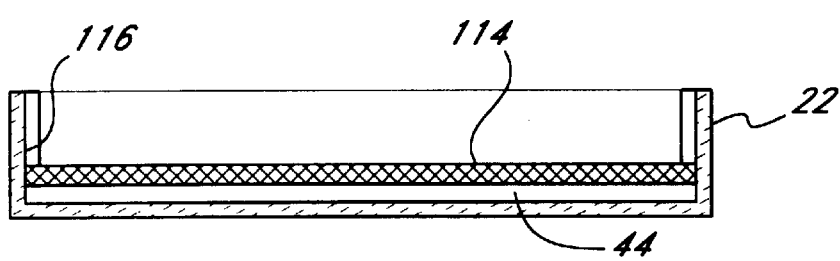
FIG. 25 shows a cross-sectional view of a culture dish containing a double hoop as in FIG. 24 into which a layer or culture medium has been poured.

As shown in FIG. 25, this provides a two-layer culture dish 22 with the two layers 44, 46 physically separated thus furnishing a perfect discontinuity for the injection of unadulterated patient blood. A wide variety of different meshes, screens, membranes or nettings can be used for this purpose. Essentially these materials provide a discontinuity between the media layers while acting as a structural reinforcement (like re-bar in concrete) to stabilize the upper layer of medium. Blood injection can be readily achieved by inserting a 19 g×$\frac{1}{8}^{th}$ inch needle through the infusion port; the 150 mm dish prepared in this fashion will accept at least 3 ml of blood. Following injection the culture dish can be incubated at body temperature (approximately 37° C.). Dishes can be placed in an anaerobic incubator or in a plastic bag with an oxygen absorbing material to facilitate the growth of anaerobic organisms. After suitable incubation (e.g., 24 hr), the dishes are examined for pathogen growth. Colonies can be isolated, transferred to another dish and "Kirby Bower" discs (containing antibiotic) can then be placed on the top surfaces of the medium and incubated for an additional 24 hr to test for antibiotic sensitivity. However, the antibiotic discs may be placed at the start of the incubation, thereby shortening the entire process greatly. This is especially effective in septicemia.

Although a number of different nettings are suitable for this process, the precision screens produced by Tetko are especially preferred. These fabrics have extremely precise openings with large percentages of open area (i.e., the strands that form the screen are very thin). For example, a preferred fabric contains 52% open area at a pore size of 105 $\mu$m. The culture dish can readily be assembled so that the infusion port dispenses the blood sample on the lower surface of the screen. By selecting much smaller pore sizes it is possible to restrict the blood cells to the lower side of the screen while serum and platelets are free to pass through to the upper surface of the screen. It is also possible to cast the two discontinuous media layers by placing a suitably-sized fabric disc on top of a hardened first layer, adding a few drops of buffer to fill the screen openings with fluid and then pouring a second medium layer on the top surface of the fabric screen. This dispenses with the double hoop but considerable care is required to avoid the fabric disc from floating free.

Figure 26:
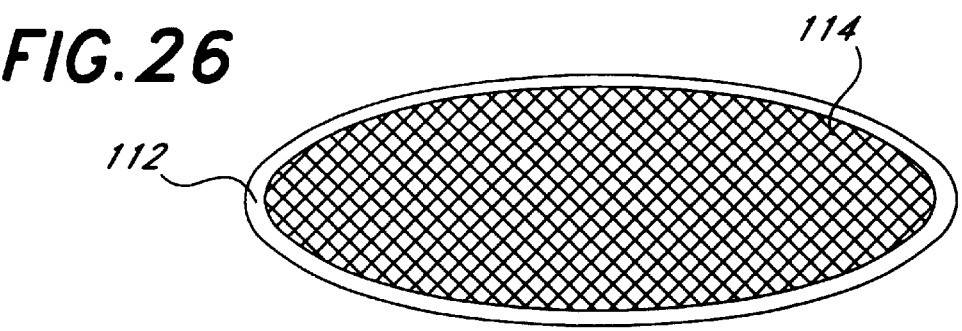
FIG. 26 shows a ring of resilient material (i.e., an O-ring) integrally molded with a layer of mesh so as to be used in place of the hoop of FIG. 24.
Figure 27:
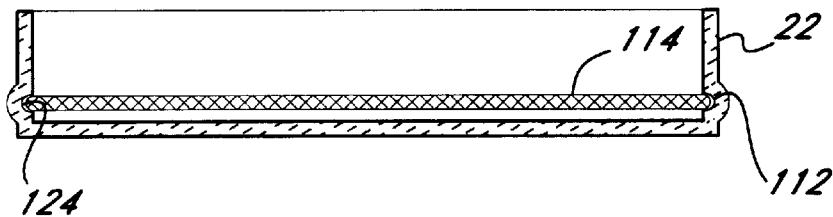
FIG. 27 shows a culture dish modified with an interior groove to accept the ring of FIG. 26.

As mentioned above a significant goal of the present device is to prevent blood from reaching the upper surface 48 by leaking along the dish wall. The hoops prevent blood leakage. It is also possible to use an O-ring or similar gasket to prevent blood leakage. For this purpose the dish may be provided with a groove for seating the O-ring. Preferably the O-ring 112 is molded integrally onto the outer edge of a fabric disk 114 (see FIGS. 26, 27). The O-ring acts like the hoops to keep the fabric taut and prevents leakage of blood up the dish walls as long as the blood is infused along the lower surface of the fabric. The O-ring may enclose a wire or plastic hoop to further ensure that the fabric is maintained adequately taut. Other fabrics (e.g., non-woven fabrics) or even semipermeable membranes can be used to divide the two culture layers. With a semipermeable membrane the blood cells and many of the pathogens will be unable to penetrate the membrane at the time of infusion. As pathogens grow they penetrate both layers but leakage to the top surface at the time of infusion must be avoided since it interferes with any specimen placed on the top surface. As mentioned, a double layer of membrane may be joined by an O-ring, which can be mounted on an inner groove of a dish. This device is particularly useful in a two lid "dish" FIG. 36 wherein access to the outer surfaces of both sides of the double membrane 131 is available. Blood is injected into the discontinuity 47 between the membranes 131 as in other embodiments of the invention. If such a membrane contains culture media no solid culture media is necessary.

Figure 28:
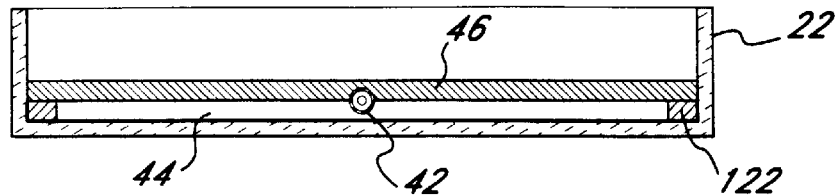
FIG. 28 shows a culture dish modified with a ledge around the peripheral edges of the bottom so that culture medium can be poured up to but not over the ledge.
Figure 29:
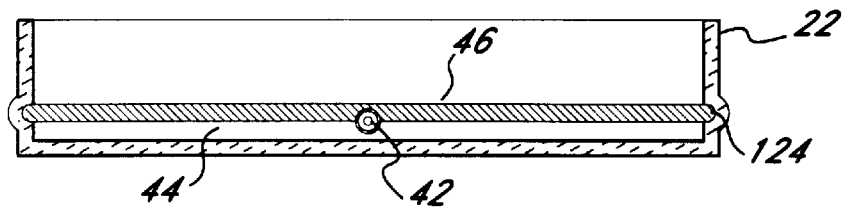
FIG. 29 shows a dish with an interior groove occupied by the second layer of culture medium so as to prevent leakage of blood up the interior lateral surfaces of the dish.
Figure 30:
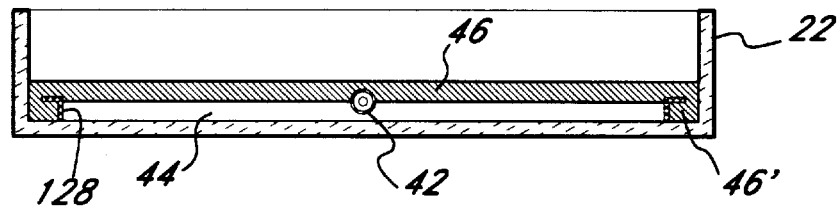
FIG. 30 shows a dish with an interior projection attached to the bottom for preventing blood leakage.
Figure 31:
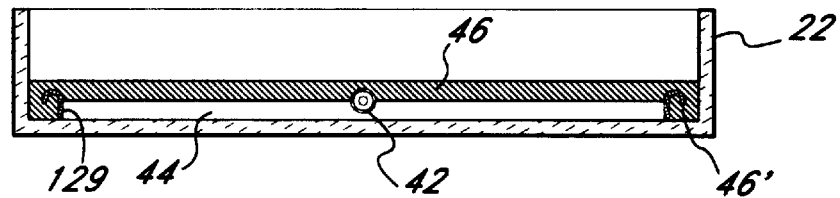
FIG. 31 shows another embodiment of the dish of FIG. 30.

The important point is that a discontinuity is formed between the two media layers to accommodate the injection of blood and that some structure is included to prevent leakage of blood along the vertical walls of the dish. FIG. 28 shows a dish 22 with a peripheral ledge 122 on its bottom. By pouring the bottom layer of culture medium 44 just up to the top of the ledge 122, the upper layer of medium 46 overlays the ledge, thereby preventing leakage of blood up the inner lateral walls of the dish 22. FIGS. 29, 30, and 31 show other structures to prevent leakage. FIGS. 30 and 31 show peripheral projections 128, 129 which function like the ledge 122 with the additional feature that a portion 46' of the upper layer of medium 46 actually "curls" behind the edges of the lower layer 44. In FIG. 29 a peripheral groove on an inner surface 124 is filled with medium of the upper layer 46, thereby preventing lateral leakage.

The layers have been described as poured agar medium. However, a number of technologies exist for growing microorganisms on various other nutrient substrates. Often cards of a clear or translucent plastic-like material (see, for example, U.S. Pat. No. 5,232,838 to Nelson et al.). These media may be dehydrated, requiring addition of water, or may be hydrated and fully functional. The discontinuous layers of the present invention can also be constructed by stacking discs of these or similar culture media or by use of membranes or fabrics.

EXAMPLE 3

Culture media is prepared in any manner typical in the art and made to flow, by any means, into a receptacle (i.e., a dish) to form a first layer. When needed, additional culture media is liquefied by being raised to room temp or higher, 35–37° C. preferred, but preferably not above 40.5° C. The liquefied culture medium, with or without additives, is mixed with freshly drawn unadulterated whole blood and then applied, by any means, to become the second layer in said receptacle. A patient specimen may, or may not, be added to the upper surface of this second layer. This now two layer melange may then be incubated at body temperature, preferably 35 to 37° C., to facilitate growth of microbes, whether in the blood or specimen, or to facilitate growth of cancer cells, lymphocytes or other leukocytes, etc. Inoculum could also be used and fresh serum may be added periodically to refresh the upper surface or the material infused into the discontinuity. Then, various chemicals or other substances may be applied for any purpose, such as testing for sensitivity to antibiotics as is well-known in the art and is described in other experiments herein. As is well known in the art, apparatus tests of this kind can be automated.

EXAMPLE 4
Container in a container e.g., bag-in-a-bag

A layer of culture media is poured into a dish and stored. As shown in FIG. 12 a bag within a bag 91 is constructed so an outer bag 92 contains an aqueous solution, e.g., isotonic saline or sterile water, etc. with or without other additives. An inner bag 94 contains dry culture media, e.g., powder, granules, etc. with or without other additives. When needed, the bags may be raised to room temperature, or to 35–37° C. preferred, but not above 40.5° C. A patient's freshly drawn and unadulterated whole blood is added to the aqueous solution in the outer bag, by injection through an infusion port 42 from a blood-filled syringe or any of the related devices illustrated and described herein. Then the blood and aqueous solution are mixed following which the inner bag is broken, releasing the powder into the outer bag which is then mixed with the blood-aqueous solution therein. Multiple inner bags can be provided, each holding different substances, so that different materials can be released into the solution at different times as needed.

The now liquid blood-culture media mixture is squeezed out or otherwise made to flow through an exit port 96 into a receptacle, or on to the surface of the first layer of culture media in a conventional culture dish. The blood-culture media mixture then gels forming a second layer similar to that in Experiment #2, above. Alternatively, the mixture may be infused between two layers of culture media, as described in Experiment #1, above. This allows any blood-borne pathogens to be encased in a special culture medium which may be useful for the culture of some "finicky" microbes. A patient specimen may or may not be added to the first layer of culture medium, to the contents of the bag, or to the surface of the second layer. The device is then adjusted for aerobic or anaerobic (e.g. purged with nitrogen) incubation as described above.

Many other variations are possible. Sterile powdered gelatin and additives may be used instead of powdered culture media in the inner bag. Granules of culture media or granules of sterile gelatin may be used to accomplish this process. Alternatively, foaming agents may be used to create a semi-solid foam as a culture medium. The bag may be constructed to avoid the risk of needle sticks to personnel in the transfer of blood into the bag (e.g., the infusion port 42 can be surrounded with an annular shield to prevent accidental needle penetration through the whole device). Also, the bag-in-a-bag device may be used as a transport device for patient blood. For this purpose more liquid may be added to keep the media from gelling in the bag, facilitating transfer to the previously described layered device upon arrival at the lab. On the other hand, liquid media that does not gel may be used. A specimen may be sent with the bag, to be later used in the layered culture device. Natural conditions of temperature, 35–37° C., without use of anticoagulants or preservatives, can thus be maintained.

The bag-in-a-bag may be used in cancer diagnosis, treatment, and research for different purposes, e.g., as a transport device for a surgically excised tumor, or portion of said tumor. The bag may contain tissue culture media, antibiotics, water or saline, etc. A tumor can be sliced into pieces with a scalpel, then a tissue grinder used to further reduce the tumor pieces to a size that will allow tumor tissue to be injected through an infusion port into the bag. Further preparation of the tumor cells may be accomplished in the bag en route to the cancer laboratory, by the addition of an enzyme such as collagenase to separate the cancer cells from supporting tissue, or by using other additives. By adding the patient's blood, growth media, etc. to the bag, refreshing the bag with the patient's serum periodically as needed, and maintaining the temp at 35–37° C. the natural conditions of the Patient Replica process may be achieved, thereby facilitating maximum survival and growth of cancer cells for later laboratory determinations.

Two bag-in-a-bags may also be used, one for patient blood to be infused between the layers of culture medium, and a second bag containing the tumor cells which will be placed upon the blood-free top layer 48, or infused between layers, depending upon tumor type, etc. An additional bag may be used to transport separated white blood cells, to be activated with Interleukin II for example, or for other diagnostic or treatment purposes. Again, the bag can have multiple compartments and/or multiple inner bags depending on the given application.

The bag(s) should be packed to be kept at 35–37° C., and transported by overnight service to any cancer laboratory in the country, arriving in condition that most closely replicates the patient's cells and chemistry, and perhaps partially prepared for study (e.g., by enzyme treatment), saving a laboratory day and allowing specific treatment to start one day earlier.

After arrival in the lab the separated cancer cells may be infused on to the top layer 48 of culture media in a layered dish with the patient's blood infused/injected between culture media layers of the dish, thereby constructing a micropathological patient replica. Alternatively the cancer cells/blood/culture media/water combination may be infused between layers of culture media in the dish, with the dish, in various embodiments, being used to test cancer cells with chemotherapeutic agents, to determine the proper dose of the most effective agent(s), or to grow patient white blood cells (T cells or B cells), treat white blood cells with additives, such as activators (Interleukin II for example), to create a vaccine, or for any other purpose. Depending on the particular goal the discontinuity 47 between layers or the surface of the culture media may be used. To refresh cancer cells with the patient's unique chemistry and nutrients fresh blood may be drawn periodically, serum separated and infused on top of the growing cancer cells, between the layers, in a broth, etc. Patient Replica conditions of no harmful additives and temp maintained between 35–37° C. are recommended.

Any container within a container can be used to accomplish this process, such as a tube-in-a-tube, or a box-in-a-box, or any combination of separate compartments which allow mixing of the separate elements when desired. Bags are preferred because their flexibility facilitates the mixing of the culture media and the blood sample. Drying agents, desiccants, may or may not be added to the inner bag (container), but such desiccants will be enclosed in a separate water permeable bag (container) and contained securely, thus ensuring that any desiccants are not released into said blood mixture when the dry powder or granules is released.

Figure 32:
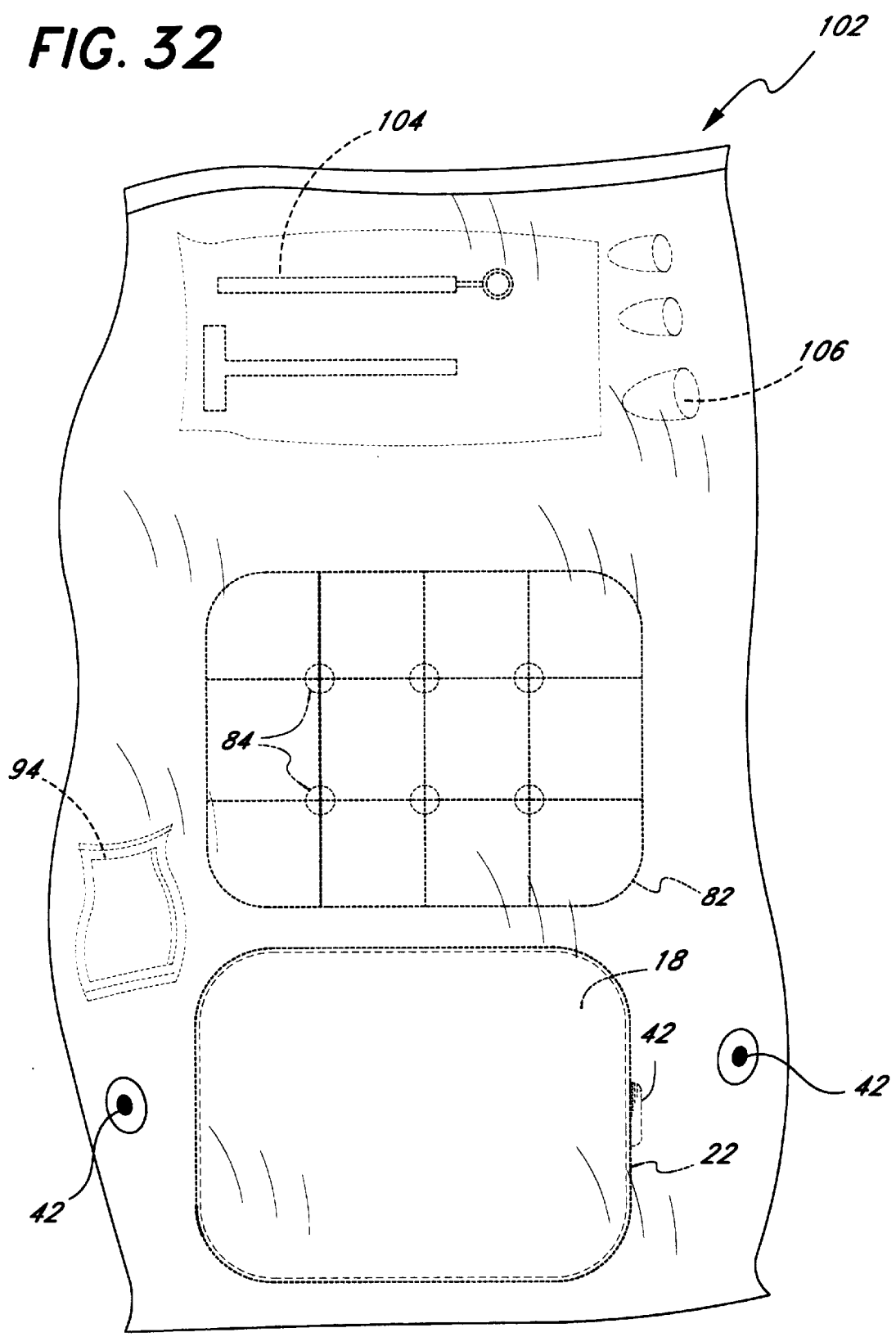
FIG. 32 shows a top view of a lab in a bag showing a layered culture dish, a testing grid and other components of the system.

There are many places in the world where unclean living conditions are part of the cause of epidemics. To culture pathogens and determine a curative antibiotic under such conditions would require a modern laboratory and highly trained personnel, and that is rarely available there. Even if available elsewhere, quarantine often prohibits sending patient specimens out. And if sent out, samples are refrigerated, preserved, etc. not in their natural conditions. The Patient Replica process and devices can be considered a "lab-in-a-box", a fully contained system, easily portable, inexpensive, that enables the determination of the cause/cure of an infectious illness, even where the air is not clean, whether in the heart of Africa, a lab in the US, or a doctor's office. As shown in FIG. 32 a layered culture dish 22 of the present invention is shown inside of a sterile "lab-in-a-bag" 102 along with a number of sterile disposable instruments 104. The lab bag 102 is sealed and sterile and is equipped with an injection port 42 through which a syringe needle can be inserted, for example, to inject blood into the layered dish 22 or to inject specimen mixed with sterile water or liquid medium. To facilitate handling of the dish 22 or the instruments 104 the lab bag 102 can be equipped with a molded thumb and finger portion 106. The lab bag is vented with a microbe filter for aerobic use and sealed for anaerobic use, optionally with Nitrogen added.

EXAMPLE 5

Double-Stoppered Tube

Figure 21:
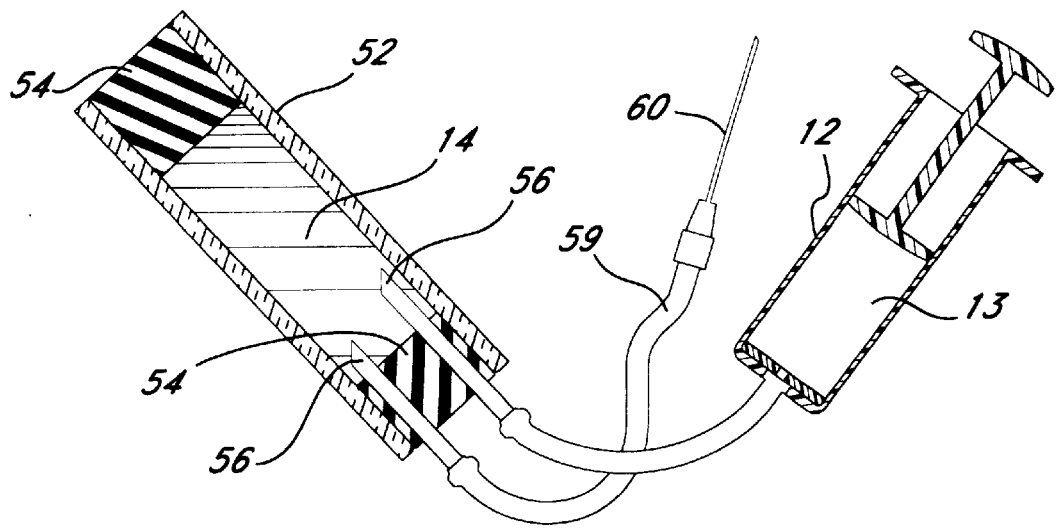
FIG. 21 shows a device similar to the one shown in FIG. 19 without a holding tube.

Blood may be drawn into a double-stoppered tube, as shown in FIG. 18, by the standard phlebotomy using a vacuum containing tube, and then transferred to a culture dish with a device such as FIG. 19–21, or by any other appropriate device. A double-stoppered tube 52 consists of a more or less cylindrical tube, preferably of glass or some optically transparent substance, with openings at either end. The openings are closed by resilient rubber stoppers 54. These stoppers may be serum caps that can be readily penetrated by a needle as is well-known in the art. In one embodiment the tube 52 contains a vacuum so that it will "suck" in blood when attached to a standard phlebotomy setup. As shown in FIG. 19, the double-stopper tube 52 can also be used with a syringe and needle arrangement (similar to FIG. 10, the single stoppered tube embodiment). FIG. 21 is also similar except that the special holding tube 58 is omitted The double-stoppered tube makes possible the design of many devices, used for a variety of purposes, e.g., to simplify blood-handling, thus increasing safety. FIG. 20 shows a combination syringe/holding tube as used in FIG. 11. Here, however, the double-stoppered tube readily permits the use of a vacuum tube blood drawing device 64 with integral needle 16. The device 64 is inserted into a vein, as is well known in the art, then an vacuum tube 52 is inserted into the device 64 with an end of the needle 16 penetrating the rubber stopper 54'. After the tube 52 fills with blood, it is inserted into the special holding tube/syringe 57 and the blood injected directly into the layered culture dish. This can be done in rapid sequence so that blood is placed into culture with essentially no passage of time.

EXAMPLE 6

Flexible Blood-Drawing Tube

Figure 22:
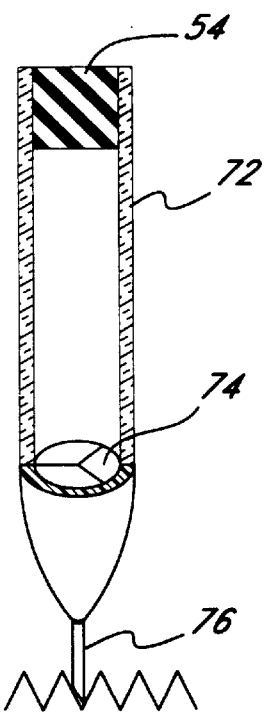
FIG. 22 shows a flexible tube for drawing blood with a single stopper and an optional valve.
Figure 23:
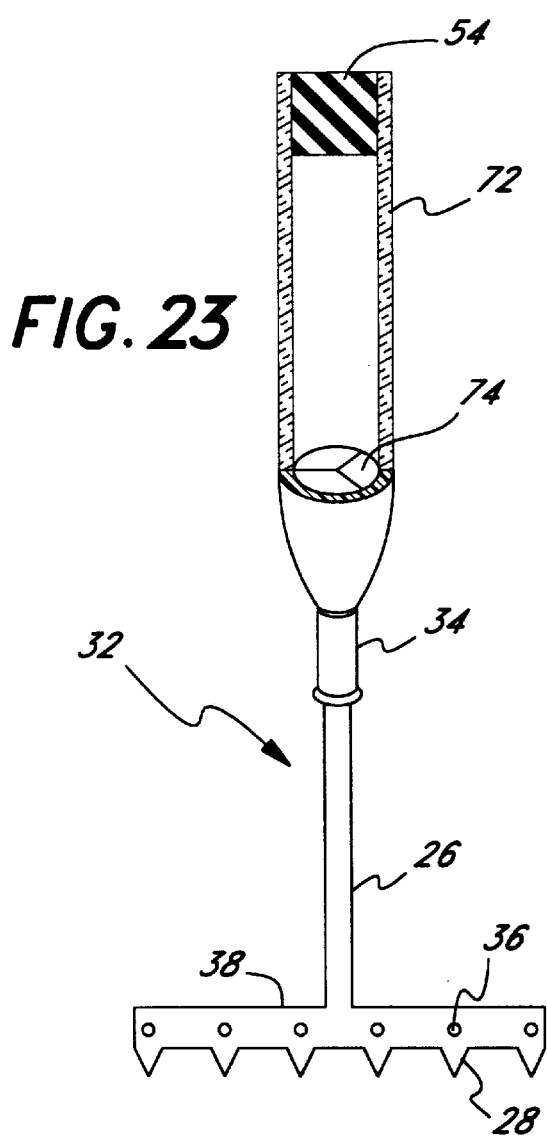
FIG. 23 shows a flexible blood drawing tube, similar to that of FIG. 22, attached to a blood-dispensing rake similar to that of FIG. 3.

Blood may be drawn into a flexible tube 72, FIG. 22, which is already connected to a culture dish by means of a dispensing tip 76 which penetrates the infusion port (not shown). This flexible tube allows the immediate expression of the blood into the attached culture dish, in a manner similar to FIGS. 4–9 and 11, thereby eliminating exposure of personnel and contamination of the media or blood. Blood is drawn into the flexible tube 74 by means of vacuum in a manner similar to the normal vacuum blood tubes already discussed. However, the tube 72 is made of a flexible, plastic material so that blood is dispensed by squeezing the tube. An optional integral valve 74 is constructed from resilient flaps rather like a heart valve and prevents inadvertent dripping of the blood. In FIG. 23 the flexible tube 72 is attached to the hollow rake 32 of FIG. 3.

EXAMPLE 7

Antibiotic Sensitivity Testing In The Physician's Office

Figure 16:
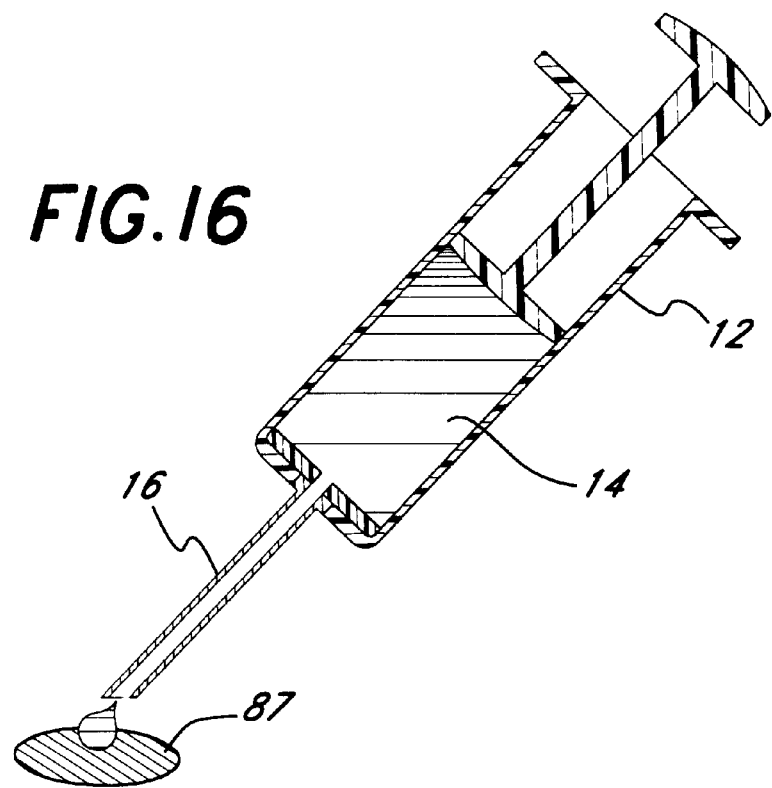
FIG. 16 shows a needle and syringe of blood being used to place a drop of blood on an antibiotic disc or on another sample.
Figure 17:
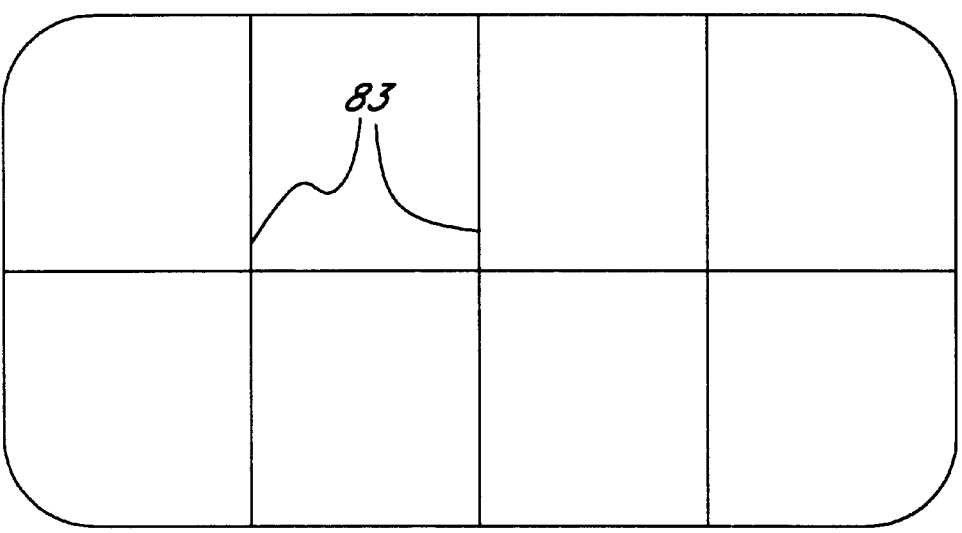
FIG. 17 shows a grid with crossing members that segment the surface of a layered culture medium of the present invention to define areas of drug sample application on the surface.

In all prior examples, a grid, FIGS. 13 and 17, may be used to place many antibiotic or other chemical samples directly upon the culture. The chemical samples can be applied in powder, pill, liquid form or on discs as is presently common in the art. FIG. 13 shows an overall view of a grid 82 intended to support antibiotic testing discs in a two-layered culture dish of the present invention. The grid is designed to fit the culture dish and at each intersection of grid crossing members 83 there is a holder 84 sized to contain a commercially available antibiotic testing disc. At shown in FIGS. 15 and 16 a cone-shaped projection 88 depends from the holder 86. The projection 88 has openings 86 in it to allow the antibiotic to diffuse into the culture medium from the discs. The cone-shaped projection 88 penetrates the top layer and can permit more direct interaction between the antibiotic sample and the sub-surface blood if needed. A zone of inhibition develops around effective antibiotic discs as is well-known in the art. In some cases advantageous results can be obtained by placing a fresh drop of patient blood directly on an antibiotic disc 87 (see FIG. 16). This is especially effective for certain aerobic pathogens which might not grow as effectively when sandwiched between the agar layers.

Figure 34:
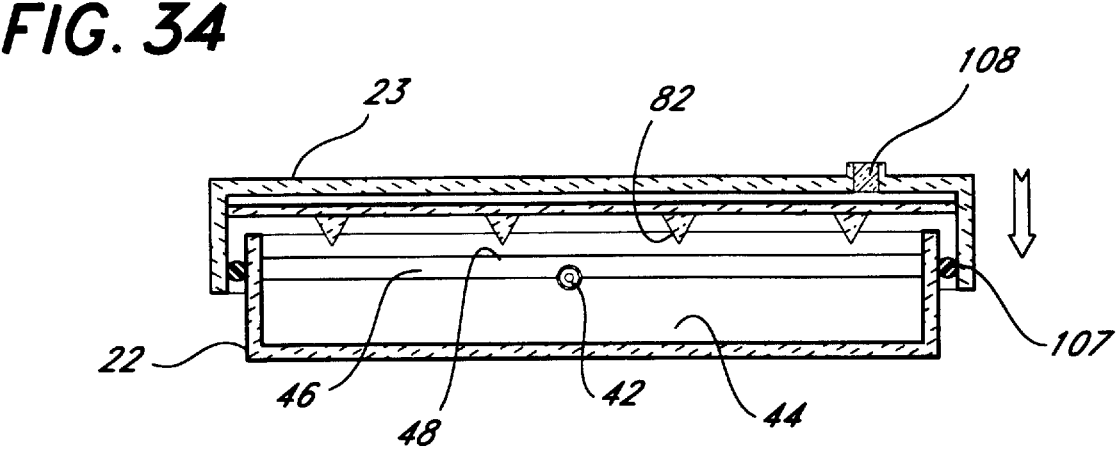
FIG. 34 shows a cross-section of a sealed culture dish of the present invention containing a testing grid that can be placed into contact with the culture medium without opening the dish.
Figure 35:
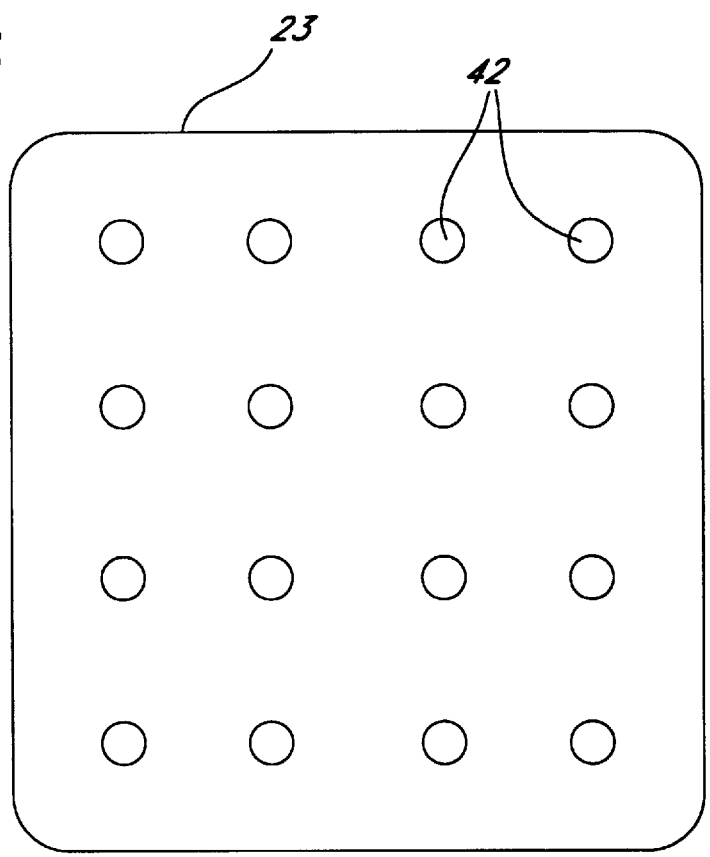
FIG. 35 shows a top view of a dish lid with a plurality of injection ports that allows injection of drug samples on to the surface of the top layer of culture medium.

The grid 82 can come prepackaged with test discs already inserted or blank holders can be used to allow addition of custom discs. An especially attractive arrangement (FIG. 34) for the physician's office comprises a layered culture dish 22 having a sealed lid (e.g. affixed with a gasket or O-ring 107 or paraffin, etc. to render the dish gas tight and not readily openable) The dish 22 is equipped with a specimen port 108 (identical in structure to the infusion port 42) and a testing grid 82 which is preloaded with a panel of antibiotic test discs. The specimen port 108 may also act as an air-lock for purging the dish 22 for anaerobic culture, etc. For aerobic culture the lid is provided with a filter that allows air but excludes microbes. The grid 22 is suspended in the lid 23 portion of the dish 22 so that it does not contact the layers of culture media 46. The device is used by infusing a fresh sample of patient blood through the infusion port 42. Either before or after such infusion a liquid patient specimen (e.g., a throat swap swirled in sterile water) may be injected through the specimen port 108 and spread over the upper surface 48 of the culture media. This injection occurs through the open grid squares of the suspended testing grid 82. At the proper time the dish 22 is manipulated to release the grid 82 so that it moves into contact with the culture medium 44. In the case of a round culture dish the grid can be suspended by projections fitting into bayonet mount type grooves. By simply twisting the dish lid 23 the grid 82 can be released. Or the grid 82 can be permanently affixed to the dish lid 23 which is held in place by an O-ring 107 between the lid 23 and the dish 22. If one presses (arrow in FIG. 34) on the lid 23, it slides down bringing the grid 82 into contact with the culture medium. In addition such a device can be included within a sterile lab-in-a-bag 102 (see FIG. 32) so that the dish 22 can be opened sterilely to allow insertion or adjustment of the grid 82. A simple grid (FIG. 17) can be used to segment the surface of the culture medium to define the area of drug application or drug samples can be inserted through ports 42 in the lid 23 as shown in FIG. 35 or onto the membrane 131 in FIG. 36.

Summary of the Safe Process

The present invention lends itself to testing procedures where there is essentially no danger of inadvertent exposure of personnel to potential pathogens. This is essential for acceptance by medical practitioners and approval by governmental organizations.

1. Provided with a kit, the physician takes a specimen (such as a throat swab), places it in a tube with sterile water and swirls to suspend any microbes present. The physician then deposits this liquid sample on the upper surface of the device of the present invention (preferably by injection through a specimen port so that the dish does not have to be opened).

Figure 33:
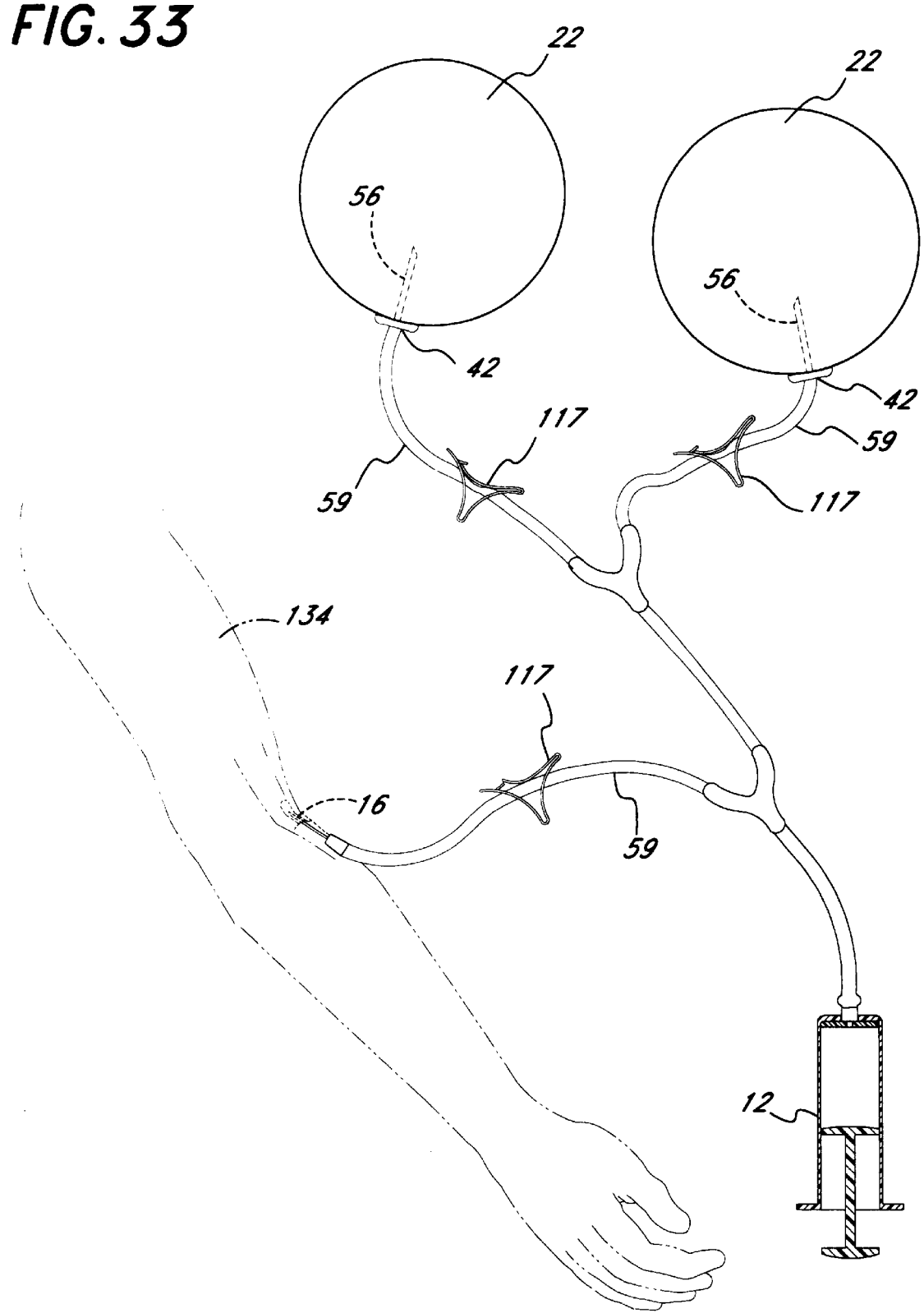
FIG. 33 shows a device for easily placing fresh blood samples into a plurality of dishes of the current invention.

2. A scalp vein set(as shown in FIG. 33) or similar device is used to obtain a patient blood sample with minimum risk of accidental exposure. A series of needles 16 attached to interconnected lengths of tubing 59 are first attached to a series of culture dishes 22 of the present invention. Preferably, at least two dishes 22 are employed (one for aerobic and one for anaerobic culture conditions). A syringe 12 is attached and the tubing 59 controlled by a number of valves 117. Finally, one of the needles 16 is inserted into a vein in the arm 134 of a patient. The proper valves 117 are opened and blood is drawn into the syringe 12. Then the valves 117 are changed permitting injection/infusion of about 3 ml of fresh blood into each of the dishes 22.

3. The blood collection apparatus is carefully discarded in a biohazard waste container.

4. The dishes are manipulated to bring an antibiotic test grid into contact with the culture medium if desired (see discussion accompanying FIG. 34).

5. The dishes are tilted to distribute the blood, if necessary, and placed in proper incubators. Either anaerobic incubators can be used for the anaerobic dish or the dish can be placed inside an anaerobic bag in a normal incubator as is well known in the art. Sample airlocks (as mentioned above) can be used to purge the anaerobic dish if desired. Sealed aerobic dishes are vented through a microbe filter.

6. After the pathogens have grown (8–24 hr), the results are interpreted without ever opening the dish, thereby eliminating danger of pathogen exposure. The dishes are then disposed of in a safe manner (e.g., autoclaved before disposal). If more detailed diagnosis is desired, the entire sealed dish can be sent to a lab for subculturing where it will be opened under perfectly safe conditions. Thus, the present invention allows rapid and sophisticated testing in the physician's office with absolutely no danger of exposure to the cultured pathogens.

The above described process of mixed culture and devices enables a physician or other personnel to determine if an antibiotic, etc. is indicated, and if so, which one(s) will be effective, while eliminating the expertise, labor, and time consuming steps of identification and isolation of pathogen (s) using the current art method of creating a pure culture. In many patients the invention will show that the proposed antibiotic is not helpful (or may actually be harmful by stimulating growth of a pathogen) so that the physician is supported in a decision not to prescribe. Similarly, the patient is supported in not demanding a useless or harmful antibiotic. The overall patient population is benefited by cost savings and by slowing the rate at which pathogens become resistant due to excessive prescription of antibiotics.

Many alterations and modifications may be made by those having ordinary skill in the art without departing from the spirit and scope of the present invention. The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself. The definitions of the words or elements of the following claims are, therefore, defined in this specification to include not only the combination of elements which are literally set forth, but all equivalent structure, material or acts for performing substantially the same function in substantially the same way to obtain substantially the same result.

In addition to the equivalents of the claimed elements, obvious substitutions now or later known to one with ordinary skill in the art are defined to be within the scope of the defined elements. The claims are thus to be understood to include what is specifically illustrated and described above, what is conceptually equivalent, what can be obviously substituted and also what essentially incorporates the essential idea of the invention. Those skilled in the art will appreciate that various adaptations and modifications of the justdescribed preferred embodiment can be configured without departing from the scope and spirit of the invention. The illustrated embodiment has been set forth only for the purposes of example and that should not be taken as limiting the invention. Therefore, it is to be understood that, within the scope of the appended claims, the invention may be practiced other than as specifically described herein.

We claim:

1. A device for culturing pathogens or cells comprising:
   a sterile container;
   a first layer of culture medium in the sterile container;
   a second layer of culture medium in contact with the first layer of culture medium but separated therefrom by a discontinuity so that the second layer of culture medium does not adhere to the first layer, the second layer having an exposed surface in contact with the atmosphere within said container;
   means for infusing an aliquot of unadulterated patient's blood into the discontinuity; and
   a layer of patient blood formed between the two layers of culture medium leaving said exposed surface of the second layer blood-free to accept a specimen.

2. The device of claim 1, wherein the sterile container is airtight and further contains a port in communication with a space above the second layer of culture medium.

3. The device of claim 2, wherein the port functions as an airlock to permit addition or removal of gases.

4. The device of claim 2, wherein the port is used for specimen injection.

5. The device of claim 2, wherein the sterile container has a top which contains a microbe air filter.

6. The device of claim 1, wherein a lid of the sterile container has a plurality of injection ports.

7. The device of claim 1, wherein the discontinuity is formed by a layer of fabric.

8. The device of claim 7, wherein the sterile container has an inner groove to accept the layer of fabric or to accept a ring holding said fabric.

9. The device of claim 1, wherein the discontinuity is formed by a layer of semipermeable membrane.

10. The device of claim 8, wherein the sterile container has an inner groove to accept the layer of semipermeable membrane or to accept a ring holding said membrane.

11. The device of claim 1 further comprising a second sterile container which encloses the sterile container.

12. The device of claim 1, wherein the means for infusing includes a tube to carry infused blood towards a central region of the layers.

13. The device of claim 12, wherein the tube has, in a wall thereof, a plurality of apertures to facilitate spread of infused blood.

14. A process for culturing pathogens or cells comprising the steps of:
    providing a sterile culture dish containing a first layer and a second layer of culture medium, the second layer in contact with the first layer and separated therefrom by a discontinuity so that the first layer does not adhere to the second layer; and an exposed surface wherein one of the layers is in contact with the atmosphere within the dish;
    injecting an aliquot of fresh unadulterated patient's blood into the discontinuity so that a layer of blood is formed between the layers of culture medium, leaving the exposed surface blood-free; and
    culturing pathogens or cells within the layer of blood or on the exposed surface.

15. The process of claim 14, wherein a sample of a patient's tumor is placed on the exposed surface.

16. The process of claim 15, wherein a sample of a patient's tumor is transported in a bag-in-a-bag device prior to use in the process.

17. The process of claim 16, wherein a sample of a patient's tumor is mixed with additives.

18. The process of claim 14, wherein cells from a patient's tumor are injected into the discontinuity.

19. The process of claim 14, wherein a patient's specimen is placed on the exposed surface so that materials diffusing from the blood layer can influence growth in the specimen.

20. The process of claim 14, wherein a drug sample is placed on the exposed surface so that material diffusing from the drug sample can influence pathogen growth.

21. The process of claim 14, wherein a grid is placed on the exposed surface to define and segment areas thereon.

22. The process of claim 14, wherein a grid apparatus is placed on the exposed surface and drug samples are placed on the grid apparatus so that material diffusing from the drug samples can influence pathogen growth in the blood layer.

23. The process of claim 22, wherein the material diffusing from the drug sample passes through apertures borne on a point projecting below the grid apparatus towards the layer of blood.

24. The process of claim 15, further comprising the step of turning the container upside down to release the layers of culture medium from the container which then provides an untouched bottom surface of culture medium.

25. The process of claim 14, wherein the steps of providing a sterile culture dish, injecting an aliquot of fresh unadulterated patient blood, incubating the dish, and inspecting the contents, is automated.

26. An improved device for culturing pathogens of the type where solid culture medium is placed in a sterile container and patient blood is added, the improvement comprising a discontinuity between a first layer of solid culture medium and a second layer of solid culture medium, means for infusing a sample of patient's blood into the discontinuity, and a layer of blood formed between the layers of the solid culture medium whereby pathogens can be cultured without adding anticoagulants to the sample of patient blood.

27. The improved device of claim 26, wherein the discontinuity is formed by a layer of fabric between the layers of solid medium.

28. The improved device of claim 26, wherein the discontinuity is formed by a layer of semipermeable membrane between the layers of solid medium.

29. The improved device of claim 26, wherein two semipermeable membranes are used for forming the discontinuity for infusion of serum, drugs or blood there between.

30. The improved device of claim 29, wherein the two membranes are held within a ring which fits within an inner groove on an inner side of a side wall, with a means to infuse liquid into the discontinuity between the membranes, and said side wall has two lids which enclose each end allowing access to either side of the two membranes within.

31. The improved device of claim 26, wherein the fabric of claim 28 is held within a ring which fits within an inner groove of said improved device.

32. The improved device of claim 26, wherein the membrane of claim 28 is held within a ring which fits within an inner groove of said improved device.

* * * * *